US012636198B2

(12) United States Patent
Maertens

(10) Patent No.: US 12,636,198 B2
(45) Date of Patent: May 26, 2026

(54) BANDAGE FOR PROVIDING PROTECTION AND ANTIMICROBIAL PROPERTIES TO A SURGICAL SITE WITH ONE OR MORE PERCUTANEOUS PINS OR WIRES

(71) Applicant: OrthoBarrier Technologies LLC, Denver, CO (US)

(72) Inventor: Andrew Maertens, Denver, CO (US)

(73) Assignee: OrthoBarrier Technologies LLC, Denver, CO (US)

( * ) Notice: Subject to any disclaimer, the term of this patent is extended or adjusted under 35 U.S.C. 154(b) by 0 days.

(21) Appl. No.: 19/242,573

(22) Filed: Jun. 18, 2025

(65) Prior Publication Data

US 2026/0000547 A1     Jan. 1, 2026

Related U.S. Application Data

(60) Provisional application No. 63/665,125, filed on Jun. 27, 2024.

(51) Int. Cl.
*A61F 13/0203* (2024.01)
*A61F 13/00* (2024.01)
(52) U.S. Cl.
CPC .... *A61F 13/0213* (2013.01); *A61F 13/00063* (2013.01); *A61F 2013/00089* (2013.01)
(58) Field of Classification Search
CPC ......... A61B 17/58; A61B 17/60; A61B 17/62; A61B 17/64; A61B 17/68
See application file for complete search history.

(56) References Cited

U.S. PATENT DOCUMENTS

| | | | | |
|---|---|---|---|---|
| 4,579,120 A | * | 4/1986 | MacGregor | ........... A61M 25/02 |
| | | | | 600/397 |
| 4,773,409 A | * | 9/1988 | Cilento | ................... A61L 15/26 |
| | | | | 428/317.1 |
| 5,447,492 A | | 9/1995 | Cartmell et al. | |
| 5,820,578 A | * | 10/1998 | Johansen | ............ A61F 13/0203 |
| | | | | 602/41 |
| 5,914,125 A | | 6/1999 | Andrews et al. | |
| 8,569,567 B2 | | 10/2013 | Ovington | |
| 8,764,714 B2 | | 7/2014 | Fabo et al. | |

(Continued)

OTHER PUBLICATIONS

Day Surgery, "Removal of K-wires (Kirschner wires): aftercare advice", East Kent Hospitals University, (Mar. 2021), pp. 1-2.

(Continued)

*Primary Examiner* — Rachael E Bredefeld
*Assistant Examiner* — Seth R. Brown
(74) *Attorney, Agent, or Firm* — Knobbe, Martens, Olson & Bear, LLP

(57) ABSTRACT

The present disclosure relates to bandages used to protect and disinfect or provide a protective antimicrobial barrier to a surgical site with one or more percutaneous pins or wires extending therefrom. The bandage includes an antimicrobial agent, an absorbent layer, an adhesive layer, and one or more slits designed to receive therethrough a percutaneous pin or wire extending from the surgical site. The bandage enhances and facilitates the ease of protecting a surgical site with one or more percutaneous pins or wires extending therefrom without disturbing the pins or wires and while protecting the surgical site from infection, contamination, and injury during the healing process.

16 Claims, 20 Drawing Sheets

(56)                    References Cited

U.S. PATENT DOCUMENTS

|  |  |  |  |  |
|---|---|---|---|---|
| 8,969,649 | B2 | 3/2015 | Leibowitz et al. | |
| 9,132,039 | B2 * | 9/2015 | Clifford ............ | A61F 13/01021 |
| 9,238,123 | B2 | 1/2016 | Weadock et al. | |
| 9,572,942 | B2 | 2/2017 | Conrad-Vlasak et al. | |
| 9,629,983 | B2 | 4/2017 | Sung | |
| 2010/0331785 | A1 * | 12/2010 | Fabo ................... | A61F 13/0203 |
| | | | | 604/180 |
| 2013/0110025 | A1 * | 5/2013 | Donnellan ........ | A61F 13/00063 |
| | | | | 602/46 |
| 2013/0131621 | A1 * | 5/2013 | Van Holten ............. | A61L 15/46 |
| | | | | 514/723 |
| 2013/0274667 | A1 * | 10/2013 | Conrad-Vlasak ..... | A61F 13/025 |
| | | | | 428/137 |
| 2016/0008576 | A1 * | 1/2016 | Lee ....................... | A61M 25/02 |
| | | | | 604/174 |
| 2016/0263351 | A1 * | 9/2016 | Schütz ................. | A61M 25/02 |
| 2020/0008981 | A1 * | 1/2020 | Wheldrake ......... | A61F 13/0209 |
| 2021/0252185 | A1 * | 8/2021 | Veruva ................. | A61L 15/225 |
| 2021/0267805 | A1 * | 9/2021 | Sanders, Jr. .......... | A61B 17/60 |

OTHER PUBLICATIONS

Ethicon US, LLC, "How to place Biopatch protective disk with CHG", Johnson-Johnson Surgical Technologies, (2022), pp. 1.
Ethicon US, LLC, "Biopatch protective disk with CHG", Johnson-Johnson Surgical Technologies, pp. 1.

* cited by examiner

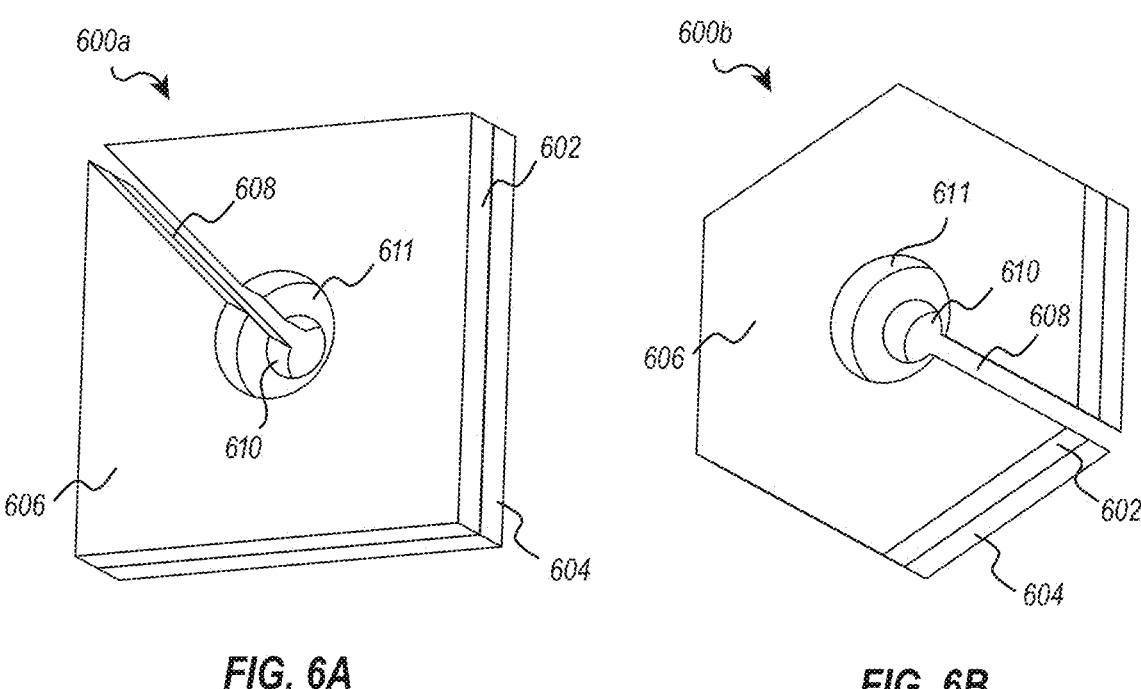
FIG. 6A
FIG. 6B
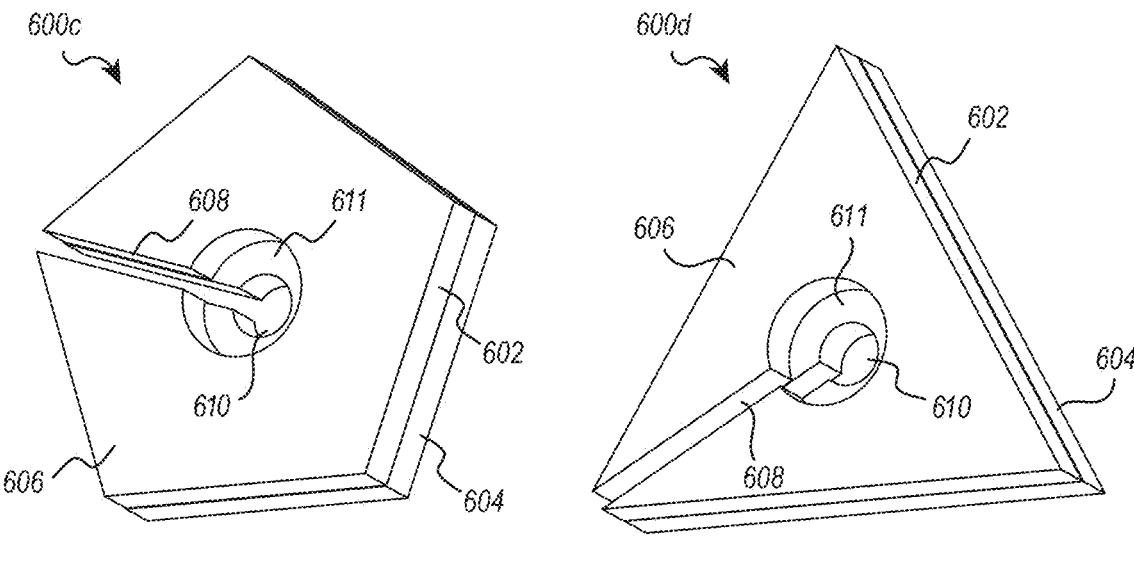
FIG. 6C
FIG. 6D

BANDAGE FOR PROVIDING PROTECTION AND ANTIMICROBIAL PROPERTIES TO A SURGICAL SITE WITH ONE OR MORE PERCUTANEOUS PINS OR WIRES

CROSS REFERENCED TO RELATED APPLICATION

This application claims the benefit of U.S. Provisional Application No. 63/665,125, filed Jun. 27, 2024, which is incorporated by reference in its entirety.

BACKGROUND

1. The Field of the Invention

The present invention relates to a wound dressings for use at the site of orthopedic and other surgical hardware, specifically percutaneous pins or wires. More particularly, the invention is directed to an integrated bandage designed to surround and protect the percutaneous pin or wire site, offering antimicrobial coverage, fluid absorption, and securement, with ease of application and circumferential sealing and protection.

2. Related Technology

In orthopedic surgery, fractures that cannot be securely immobilized with a cast often require the use of percutaneous fixation devices such as Kirschner wires (K-wires), Steinmann pins, or external fixation pins configured to maintain bone alignment. During surgery, surgical pins or wires are inserted through the skin into bone following fracture reduction and are left in place for either a temporary (hours or days) or an extended period of time (weeks to months) to promote osseous stability and eventual union. The external or protruding portion of percutaneous pins and wires facilitate their eventual removal but also penetrates through the skin, creating a direct pathway for microbial entry and increasing the risk of pin site infections (PSIs).

In many situations, percutaneous pins and/or wires will protrude from the skin after they are inserted and used to hold a fractured bone together. This facilitates their removal once the bone has healed sufficiently. Accordingly, the percutaneous pins and/or wires are often left in place for extended periods (e.g., 2 weeks to 4 months). This skin penetration and external nature of the construct creates a serious risk of infection, which necessitates effective wound care to prevent infections.

FIG. 1 schematically illustrates a surgical site 100 comprising a skin surface 102, a percutaneous surgical pin/wire 104 extending outwardly from the skin 102, a wound 106, and wound exudate 108 (e.g., blood, blood components, plasma, serum, and/or serosanguineous discharges). As illustrated, the percutaneous surgical pin/wire 104 is bent to form a Shepard's crook in order to limit the protrusion distance from the skin and prevent the pin or wire from migrating under the skin surface.

FIG. 2 illustrates an example of a surgical site 200 of a badly damaged finger that has been surgically repaired using a plurality of percutaneous surgical pins or wires 204 that protrude from the skin 202 and are interconnected with a cage-like structure, a plurality of wounds 206, and wound exudate 208. The wounds 206 around the surgical pins or wires 204 are unprotected and a direct pathway for microbes to enter and infect the surgical site. Moreover, the surgical pins or wires 204 are interconnected, which complicates placement of protective bandages.

Current wound care solutions can be ad hoc and are often inadequate in preventing infection and managing wound exudate. In particular, percutaneous pins and/or wires impede proper placement of traditional wound bandages or dressings known in the art. Instead, traditional bandages must be modified by the surgeon or other medical practitioner, combined, and/or secured with external adhesive means, such as medical tape or glue, in order to protect and/or disinfect the surgical site around the protruding percutaneous pins and/or wires. Furthermore, medical practitioners and/or patients attempting to apply modified wound bandages must do so without disturbing the percutaneous pins and/or wires. Also, because traditional wound bandages are not designed for use with surgical pins, they may not reliably remain in place and/or may not provide adequate protection of the surgical site. In addition, modification of existing bandages may take prolonged time, produce errors, and make the process of protecting the surgical site more difficult and less reliable. This can be particularly problematic if the patient wishes to remove old or dirty wound dressings and replace them with fresh ones on a regular basis without proper training.

FIG. 3, for example, illustrates an example of a surgical site 300 of a foot (lower extremity) that has been surgically repaired using a plurality of percutaneous surgical pins 304 that protrude from the skin 302 and are attached to an external stabilization structure (also known as external fixator) 305, which can complicate placement of bandages. The wounds around the surgical pins 304 have been covered with makeshift bandages using typical gauze wrap and a petroleum gauze 310. One will appreciate the challenge presented to a medical practitioner when trying to provide wound care to such a surgical site. For instance, FIG. 3 illustrates the cumbersome nature of wrapping each wound and corresponding surgical pin 304 with gauze 310 in the presence of the external fixator device. Because the gauze 310 needs to be changed periodically, such difficulties will persist until the surgical pins 304 are removed and may be particularly difficult where the patient is required to change the makeshift gauze bandages on their own at home.

Commercially available dressings—such as antimicrobial foams containing agents like chlorhexidine gluconate—offer some benefit but are not specifically engineered for use at orthopedic surgical pin or wire sites. Many such products lack an adhesive layer and/or structural features to facilitate secure and reliable circumferential placement around a pin or wire, limiting their effectiveness. Multi-step dressing systems requiring separate application of foam and transparent film, adhesive or tape layers do not appropriately accommodate a vertically oriented pin or wire. They also introduce complexity, potential contamination, and longer exposure of the site during dressing changes. Again, this can be particularly problematic if the patient wishes to remove old or dirty wound dressings and replace them with fresh ones.

Therefore, there is a need for a purpose-built, integrated wound dressing system that is specifically tailored to the unique requirements of orthopedic and surgical pin or wire sites.

SUMMARY

The present invention addresses the foregoing challenges by providing a protective adhesive dressing or bandage (collectively "bandage") that includes an adhesive and antimicrobial absorbent pad and an integrated slit or aperture to facilitate placement around a percutaneous pin or wire protruding from the skin at a surgical site. The disclosed bandage combines antimicrobial activity, absorbent properties, and secure adhesion in a single unit, with a slit that facilitates application around an exposed pin or wire without disturbing the implant or surgical site. This configuration facilitates quick and secure placement around percutaneous pins or wires, while ensuring comprehensive protection, enhanced ease of use, and reduced risk of infection. It is particularly beneficial as a time saving means for surgeons and medical practitioners, and for patients when it is desired to remove old or dirty wound bandages and replace them with fresh ones.

Accordingly, the present application satisfies the need for wound bandages that are specifically engineered to provide antimicrobial protection, absorb exudate, and promote healing around percutaneous pins and wires at a surgical site. The present invention is directed to novel—yet simple to use—wound care bandages designed specifically for percutaneous pins and/or wires. Such bandages may comprise a layered structure that provides the combination of antimicrobial properties, exudate absorption, and mechanical stability (i.e., through adhesion). The bandage includes a slit that passes partially across the width or diameter of the bandage to facilitate circumferential placement around a protruding pin or wire and an adhesive border or layer to secure the bandage in place at the surgical site. The disclosed surgical dressings are designed to reduce the risk of infection, improve patient comfort and compliance, facilitate easier wound monitoring and care, and facilitate removal and replacement of old or dirty bandages with fresh bandages, including by healthcare practitioners and patients.

In a first embodiment of a bandage for providing wound care at a surgical site with a percutaneous pin or wire, the bandage comprises an adhesive layer, an absorbent layer, an antimicrobial material forming a layer (e.g., between the adhesive and absorbent layers) and/or that is impregnated in the adhesive layer and/or the absorbent layer, and a slit configured to facilitate placement of the bandage around a percutaneous pin or wire. The slit may lead to or terminate at a central opening, which may be selected to correspond to the diameter of the percutaneous pin or wire to ensure good circumferential contact of the absorbent material of the layer around the pin or wire.

A first side of the adhesive layer is configured to adhere to tissue, and a second side opposite the first side is configured for adhesion of the absorbent and/or antimicrobial layer. The adhesive layer may comprise, as nonlimiting examples, a hydrocolloid, acrylic polymer film, cyanoacrylate film, silicone film, and/or other material capable of attaching to skin at a surgical site. The bandage further includes a backing layer adjacent to the first side of the adhesive layer to protect the adhesive (such as to prevent contamination and/or self-adhesion) prior to use. In some embodiments, the adhesive layer facilitates attachment of the bandage to tissue and/or the percutaneous pin or wire at the surgical site without the use of tape.

The bandage further includes an absorbent layer adjacent (e.g., adhered) to the second side of the adhesive layer. In some embodiments, the absorbent layer is configured to absorb fluids (e.g., blood, plasma, serum, and/or serosanguineous discharges that may leak from the surgical site). The absorbent layer may advantageously comprise a porous and/or hydrophilic material formulated and be configured to absorb fluids (exudate) discharged from the surgical site, including at the interface of patient tissue and the percutaneous pin or wire. Non-limiting examples include silicone, cotton wool, gauze, lint, plasters, foam, alginate, hydrocolloid, hydrogel, and or others capable of absorbing fluid leakage from a surgical or other wound site.

The absorbent layer may optionally be impregnated with a hemostatic agent. In some embodiments, the hemostatic agent may comprise one or more of thrombin, thrombin enzyme, prothrombin complex concentrate, dried plasma, cyanoacrylate, fibrin sealant, tranexamic acid, microfibrillar collagen, microporous polysaccharide spheres, gelatin matrix, oxidized regenerated cellulose, alginate, albumin, glutaraldehyde, alum (hydrated salts of aluminum and alkali metals), aluminum chloride, zinc chloride, and ferric sulfates.

The bandage further includes an antimicrobial agent impregnated in or positioned adjacent to at least one of the adhesive layer or the absorbent layer. In some embodiments, the antimicrobial agent in the antimicrobial layer and/or impregnated in the absorbent layer and/or adhesive layer, is configured to provide antimicrobial protection at the surgical site. The term "provide antimicrobial protection" can broadly mean any antiseptic activity in which microbes and biofilms are killed, destroyed, and/or prevented from forming at and/or proliferating and infecting the surgical site. In some embodiments, the antimicrobial agent may include, but is not limited to, one or more of silver (e.g., silver nanoparticles and silver salts, such as silver nitrate and silver sulfadiazine, ionic silver, and nanocrystalline silver), iodine (e.g., povidone iodine and cadexomer iodine), chlorhexidine (e.g., chlorhexidine gluconate), polyhexamethylene biguanide (PHMB), honey, antibiotics (e.g., gentamicin, mupirocin, and bacitracin), hypochlorous acid, gentian violet, and essential oils (e.g., tea tree oil).

The bandage further includes a slit passing partially across the width or diameter of the bandage, preferably through each layer of the bandage. The slit is configured to facilitate circumferential placement of the bandage around and accommodate a percutaneous pin or wire passing through the bandage in a desired position. In some embodiments, the slit may pass approximately halfway across the diameter or width of the bandage, although it can be more or less than halfway as desired to accommodate a surgical site. The absorbent layer may be configured to circumferentially contact and close around the pin or wire to provide an antimicrobial barrier and absorb exudates from the wound.

In some embodiments, the bandage has a height or cross-sectional thickness in the range of about 0.1 cm to about 10 cm, or about 0.2 cm to about 8 cm, or about 0.5 cm to about 5 cm. The adhesive layer may have a relatively small cross-sectional thickness, such in the range of about 0.1 mm to about 2 mm, or about 0.2 mm to about 1 mm, with the majority of the height or cross-sectional thickness of the bandage comprising or being provided by the absorbent layer. In some embodiments, the bandage has a diameter or width in the range of about 0.5 cm to about 12 cm, or about 0.75 cm to about 10 cm, or about 1 cm to about 8 cm, or about 1.5 cm to about 6 cm, or about 2 cm to about 5 cm. In some embodiments, the bandage can have a desired geometric shape. For example, the bandage may be circular, rectangular, triangular, pentagonal, hexagonal, or octagonal. The geometric shape of the bandage may facilitate the placement of a plurality of bandages at a surgical site that has more than one exposed percutaneous pin or wire. In some implementations, a plurality of bandages having advantageous geometric shapes can be arranged to form an uninterrupted barrier at the surgical site.

In an alternative embodiment, a bandage for providing wound care at a surgical site with one or more percutaneous pins or wires comprises an adhesive layer with a first side configured to adhere to tissue and a second side opposite the first side. The bandage further includes a backing layer adjacent to the first side of the adhesive layer and an absorbent layer adjacent to the second side. The bandage further includes an antimicrobial agent in and/or adjacent to at least one of the adhesive layer or the absorbent layer. The bandage further includes a plurality of slits passing through the bandage (i.e., passing partially across the width or diameter and through each layer of the bandage). The plurality of slits are configured to accommodate a plurality of percutaneous pins or wires received therethrough. Alternatively, the plurality of slits may simply provide a plurality of locations that can best accommodate a percutaneous pin or wire at a given location at the surgical site.

A method of protecting and providing an antimicrobial barrier at a surgical site with one or more percutaneous pins and/or wires extending therefrom comprises providing one or more bandages comprised of an adhesive layer, an absorbent layer, and a antimicrobial agent forming a separate layer and/or impregnated in the adhesive layer and/or absorbent layer, and one or more slits extending partially across the width or diameter of the bandage and through the adhesive layer, antimicrobial agent, and absorbent layer. The method further involves removing a backing layer from a first side of the adhesive layer and placing the adhesive layer at the surgical site such that each of the one or more percutaneous pins or wires extends through a respective slit of one or more bandages. The absorbent layer absorbs any fluids or exudate that may leak out of the surgical site, including the wound caused by the percutaneous pin or wire, and the antimicrobial agent disinfects the surgical site (e.g., maintains a sterile environment at the surgical site by providing an antimicrobial barrier).

These and other advantages and features of the invention will become more fully apparent from the following description and appended claims or may be learned by the practice of the invention as set forth hereinafter.

BRIEF DESCRIPTION OF THE DRAWINGS

In order to describe the manner in which at least some of the advantages and features of the invention may be obtained, a more particular description of embodiments of the invention will be rendered by reference to specific embodiments thereof which are illustrated in the appended drawings. Understanding that these drawings depict only typical embodiments of the invention and are not therefore to be considered to be limiting of its scope, embodiments of the invention will be described and explained with additional specificity and detail through the use of the accompanying drawings.

FIG. 4A is a top perspective view and FIG. 4B is a side cross-sectional view that schematically illustrate a first embodiment of a bandage designed to protect and provide an

Figure 5A:
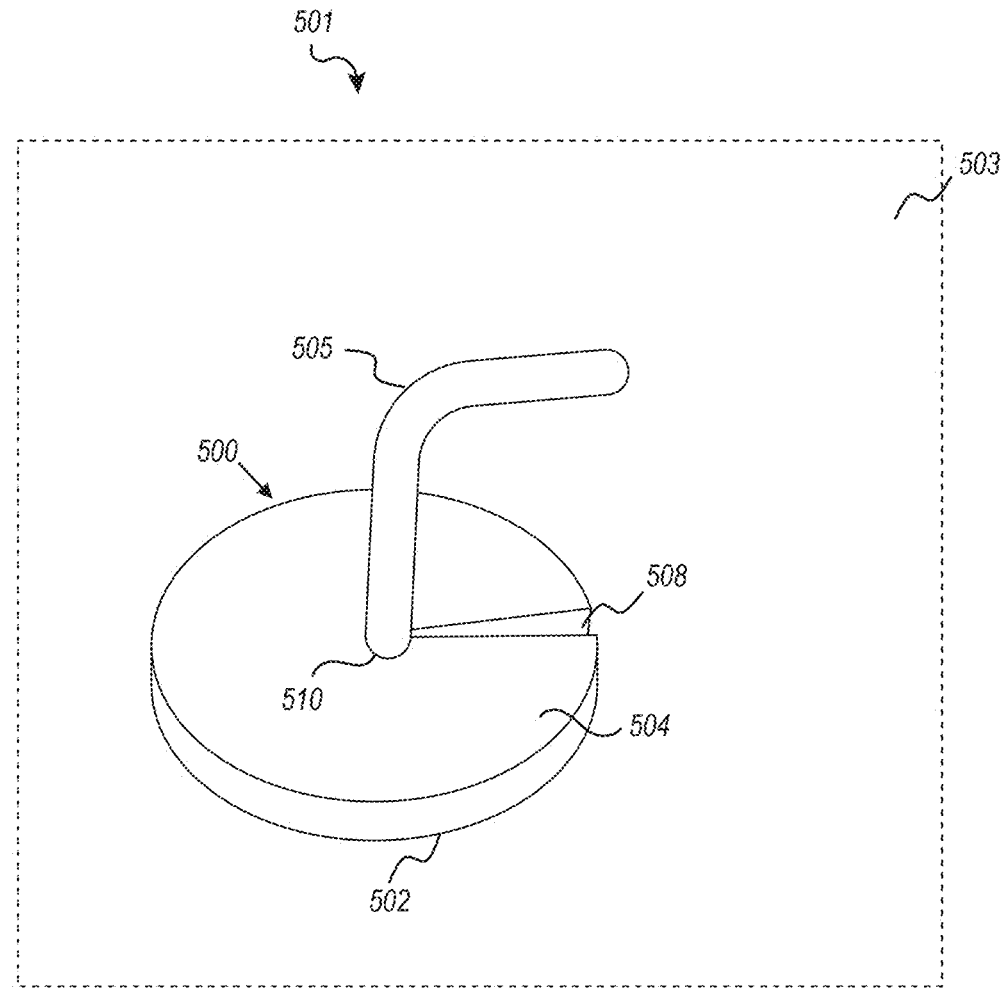
Figure 5B:
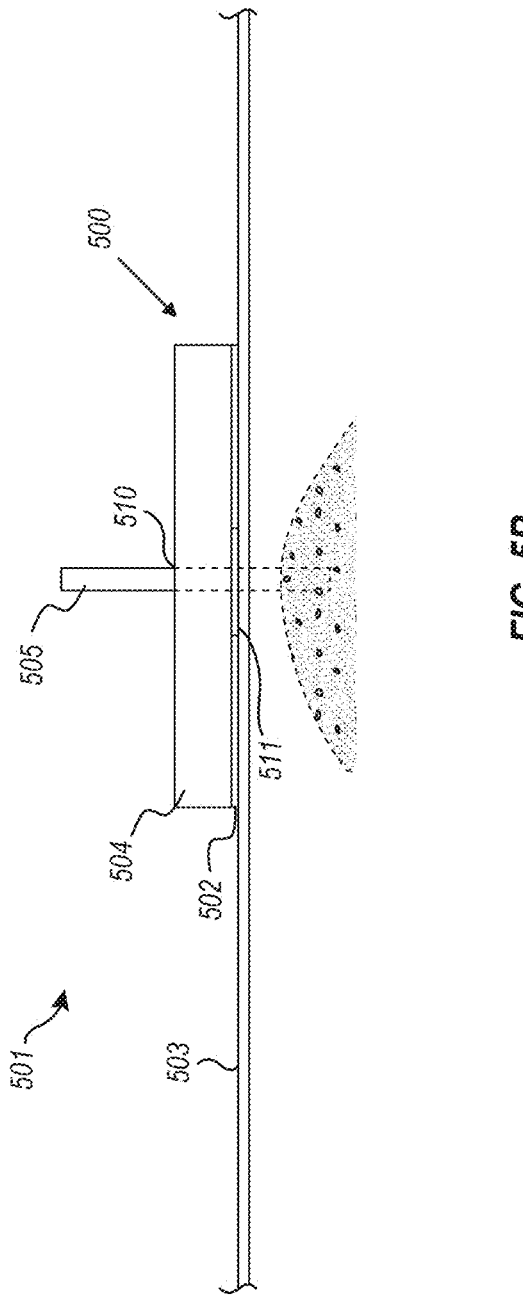
Figure 7A:
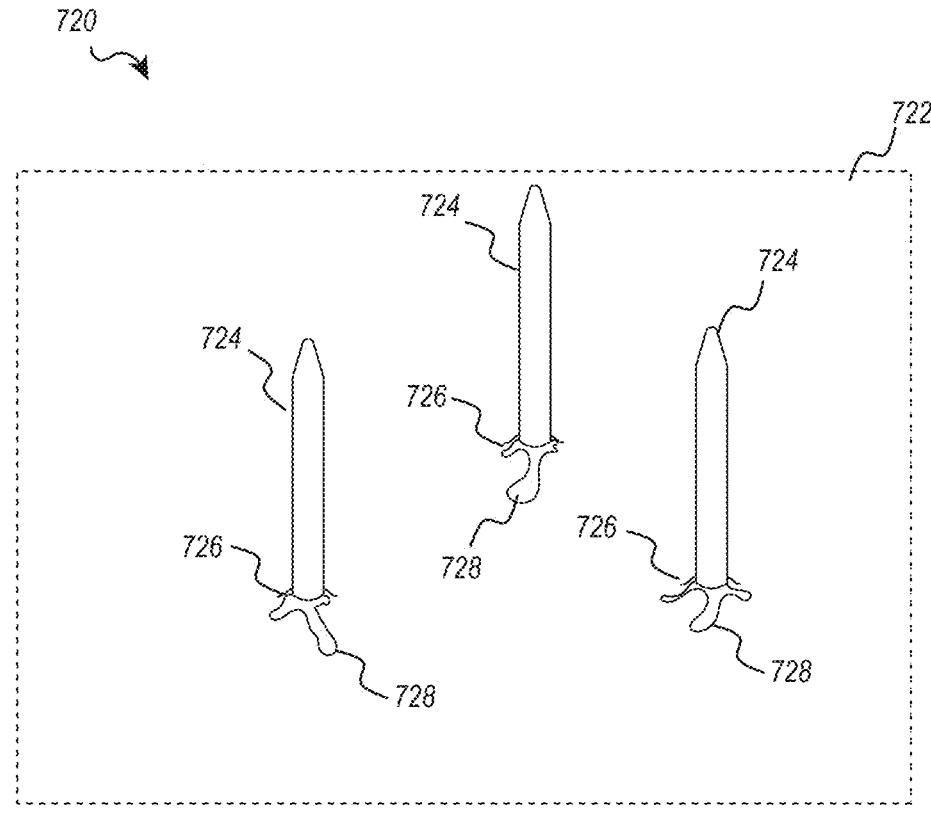
Figure 7B:
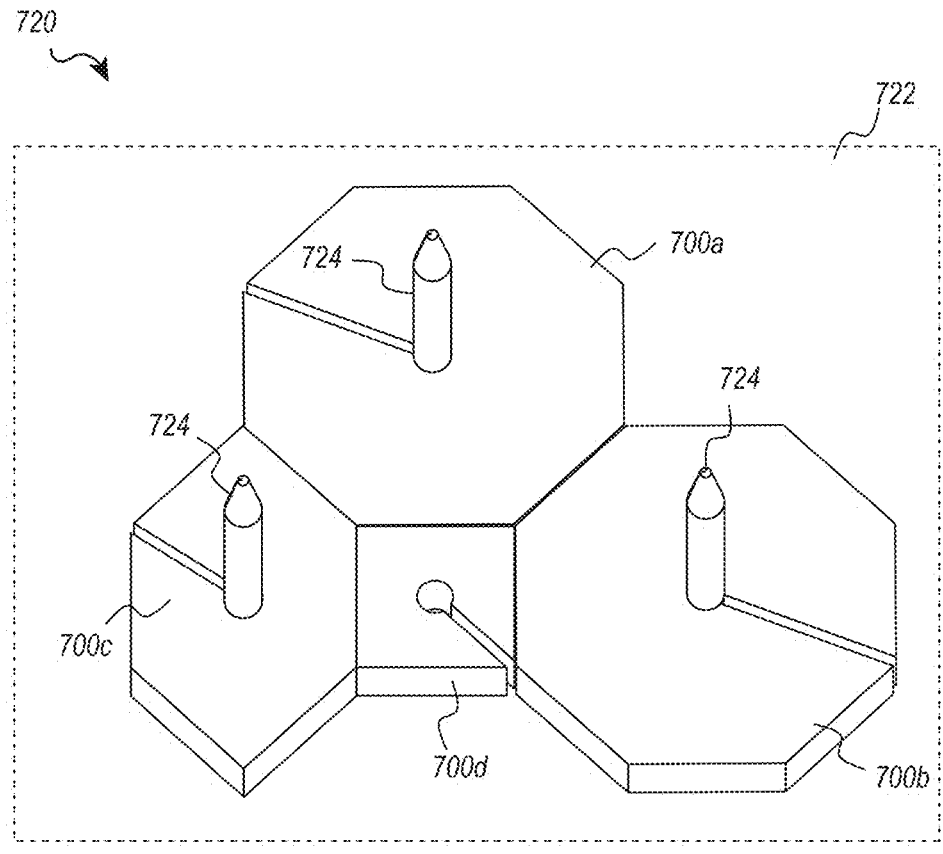
Figure 8A:
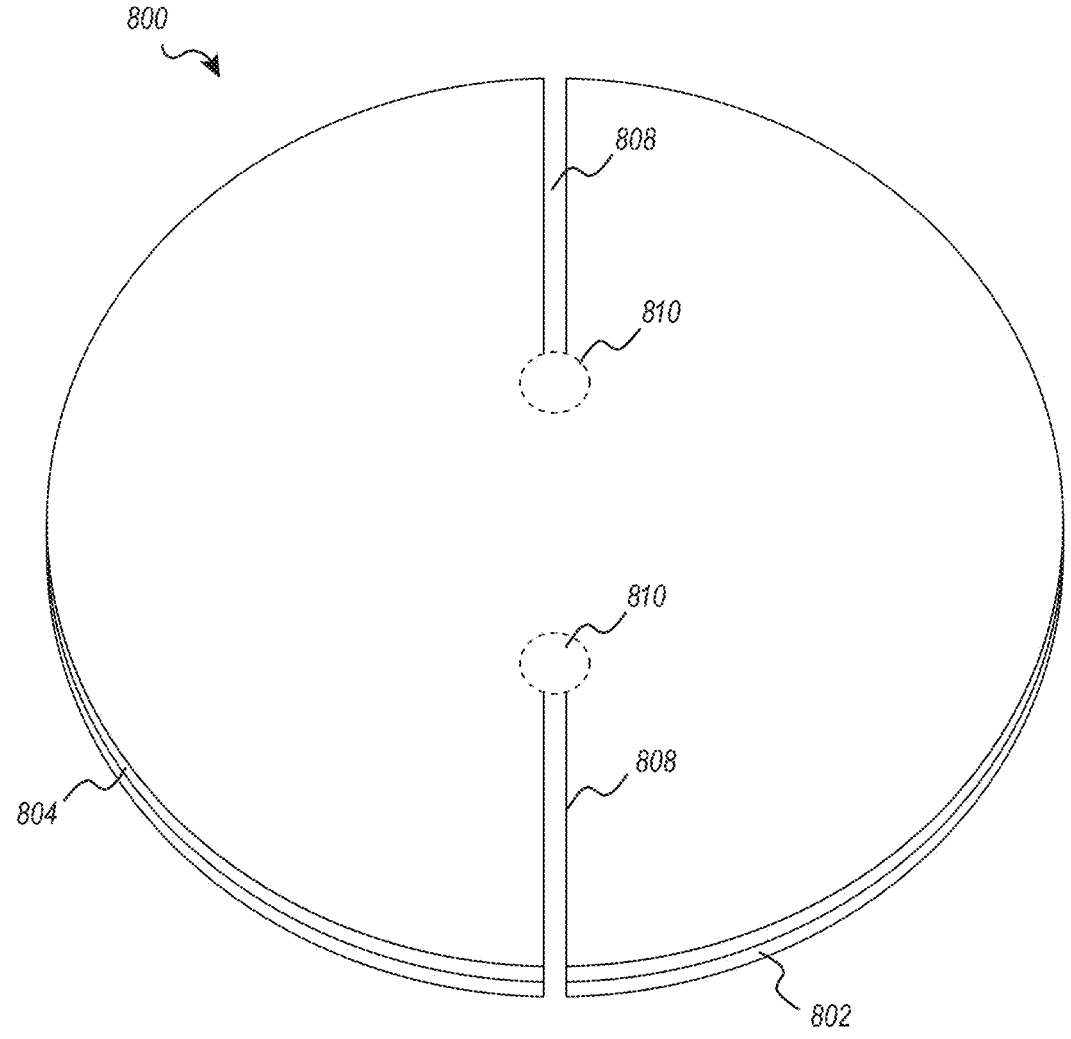
Figure 8B:
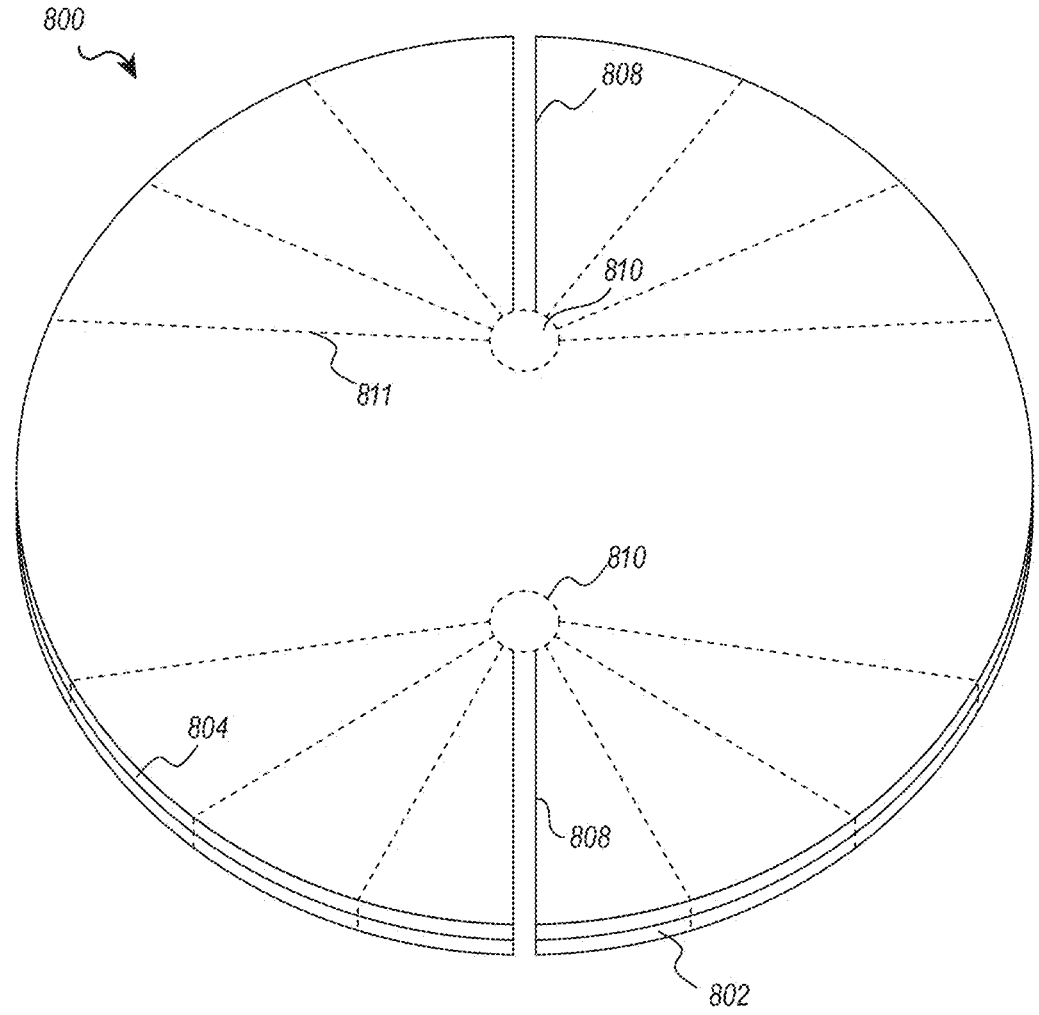
Figure 9:
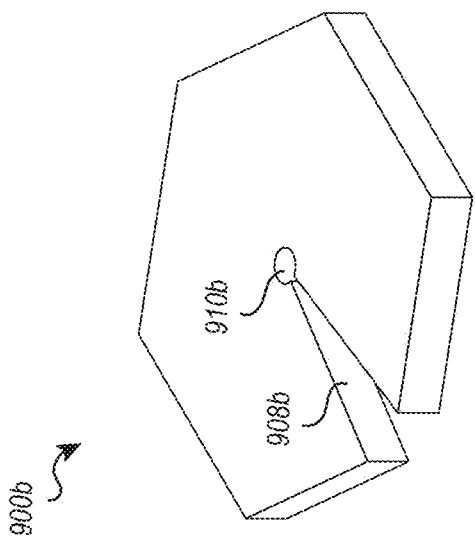
Figure 9:
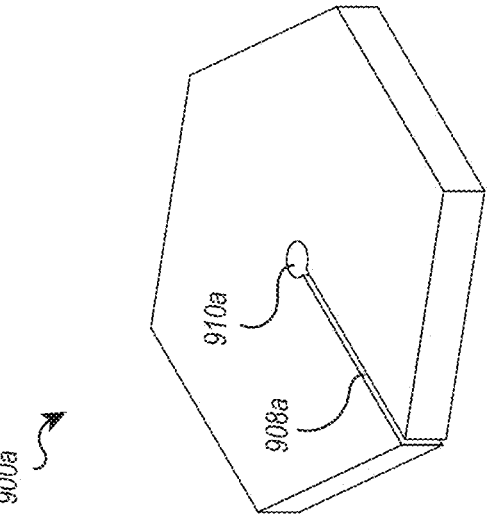
Figure 10:
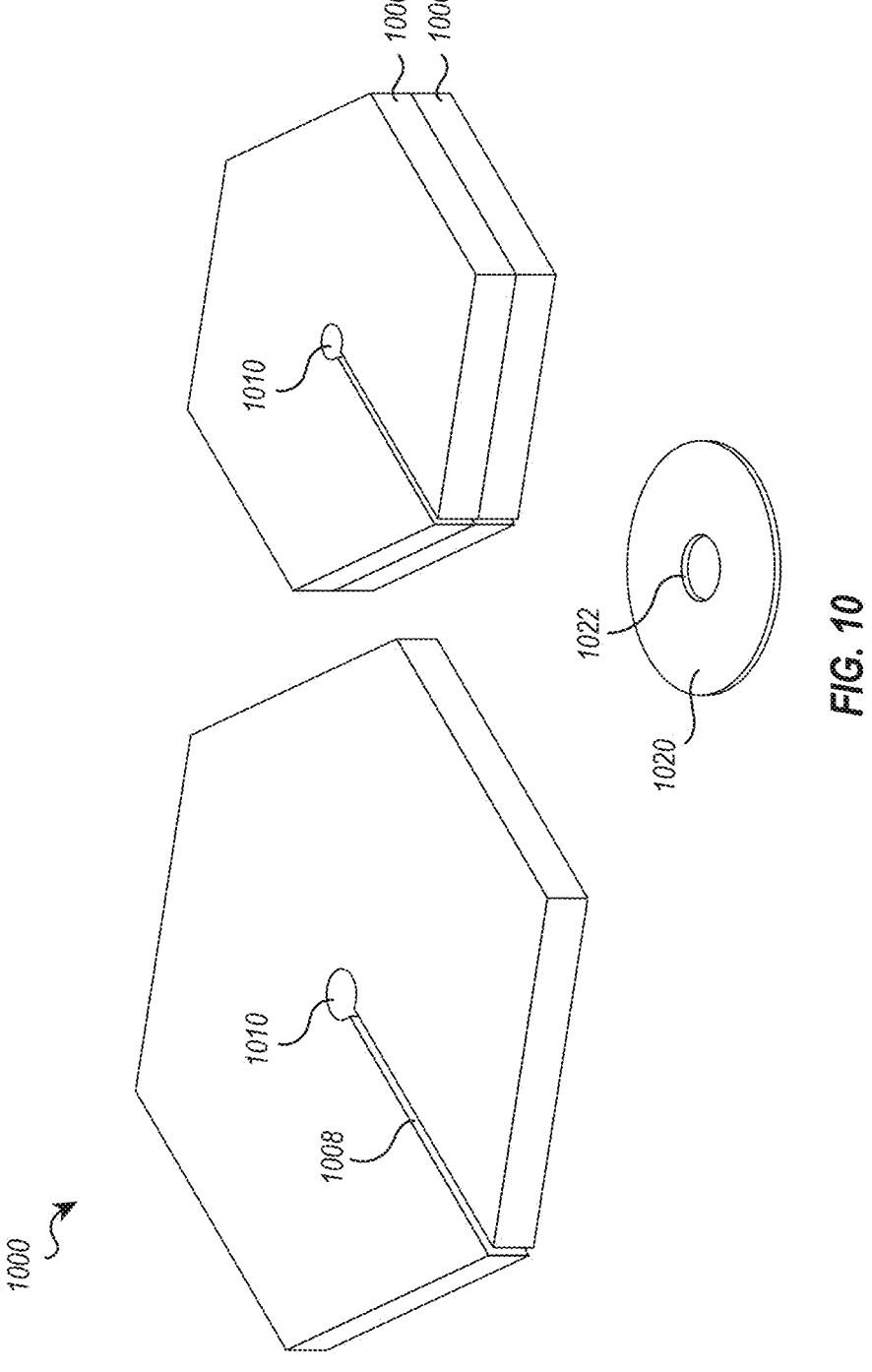
Figure 11:
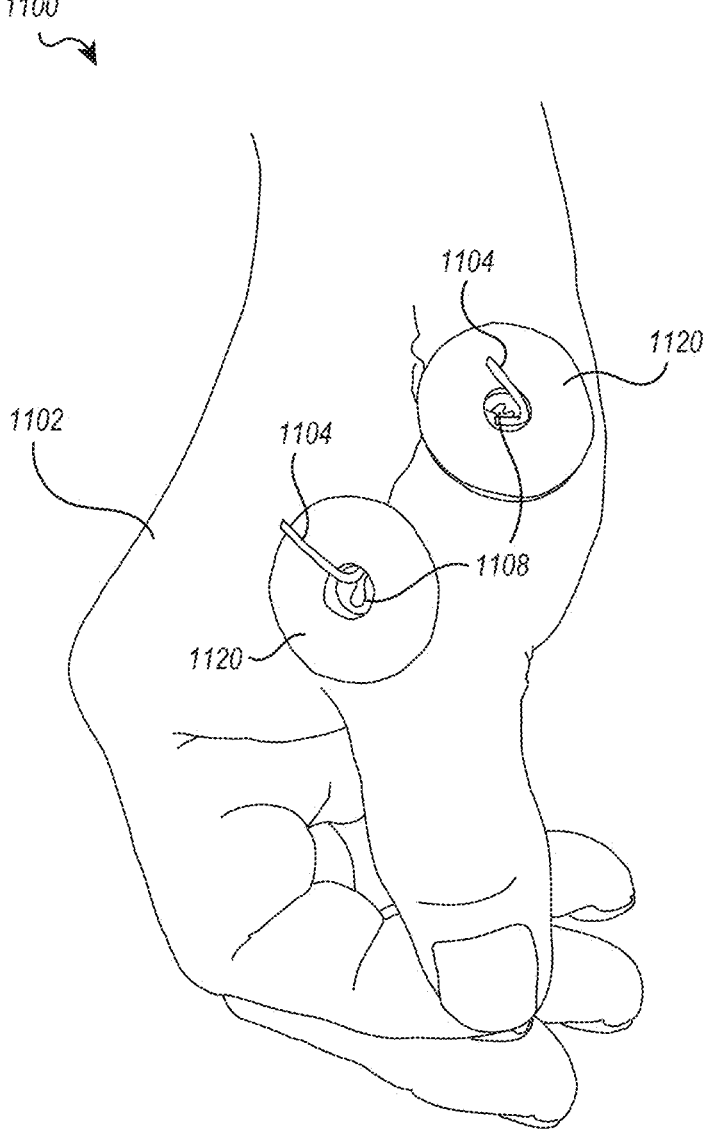
Figure 12:
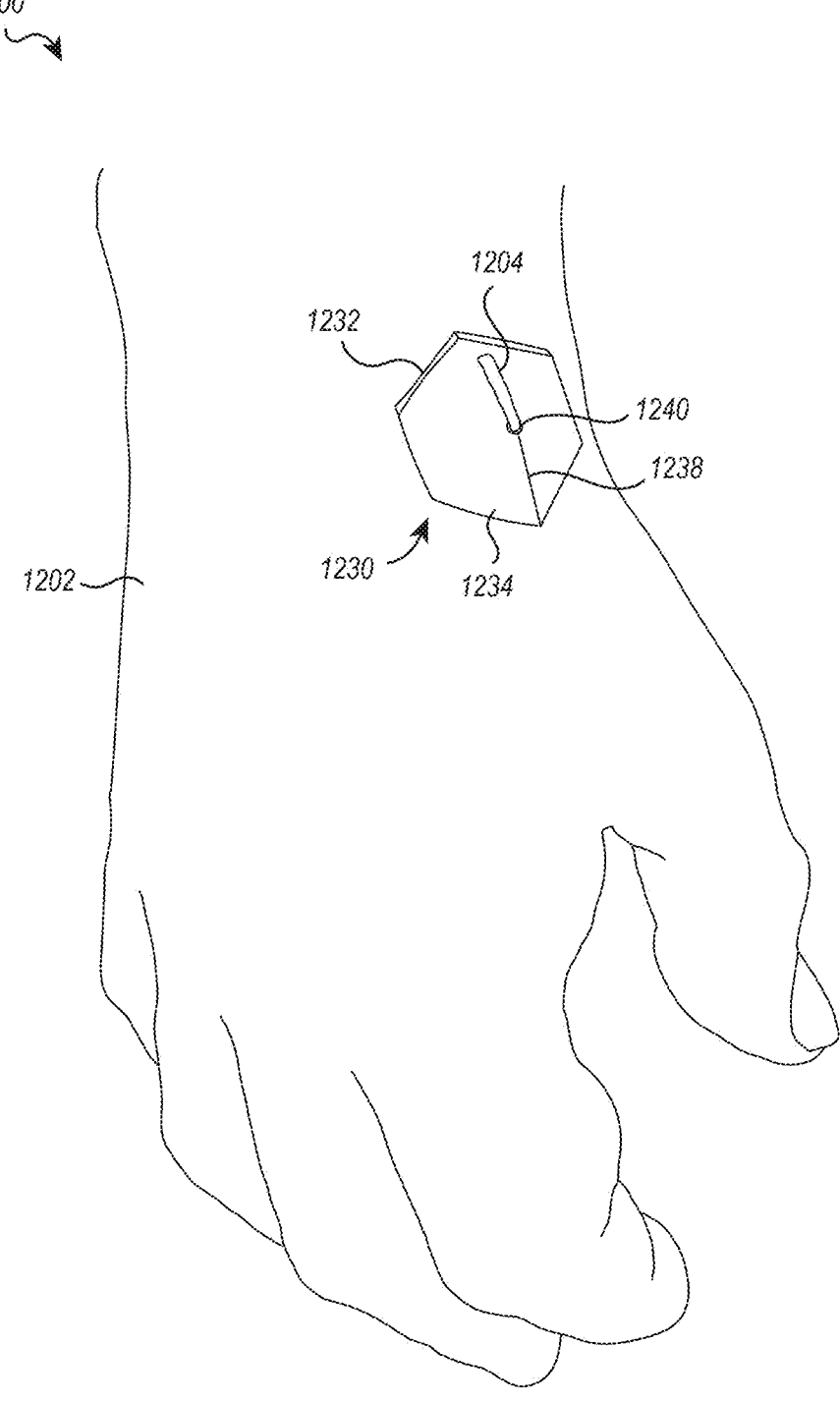
Figure 13:
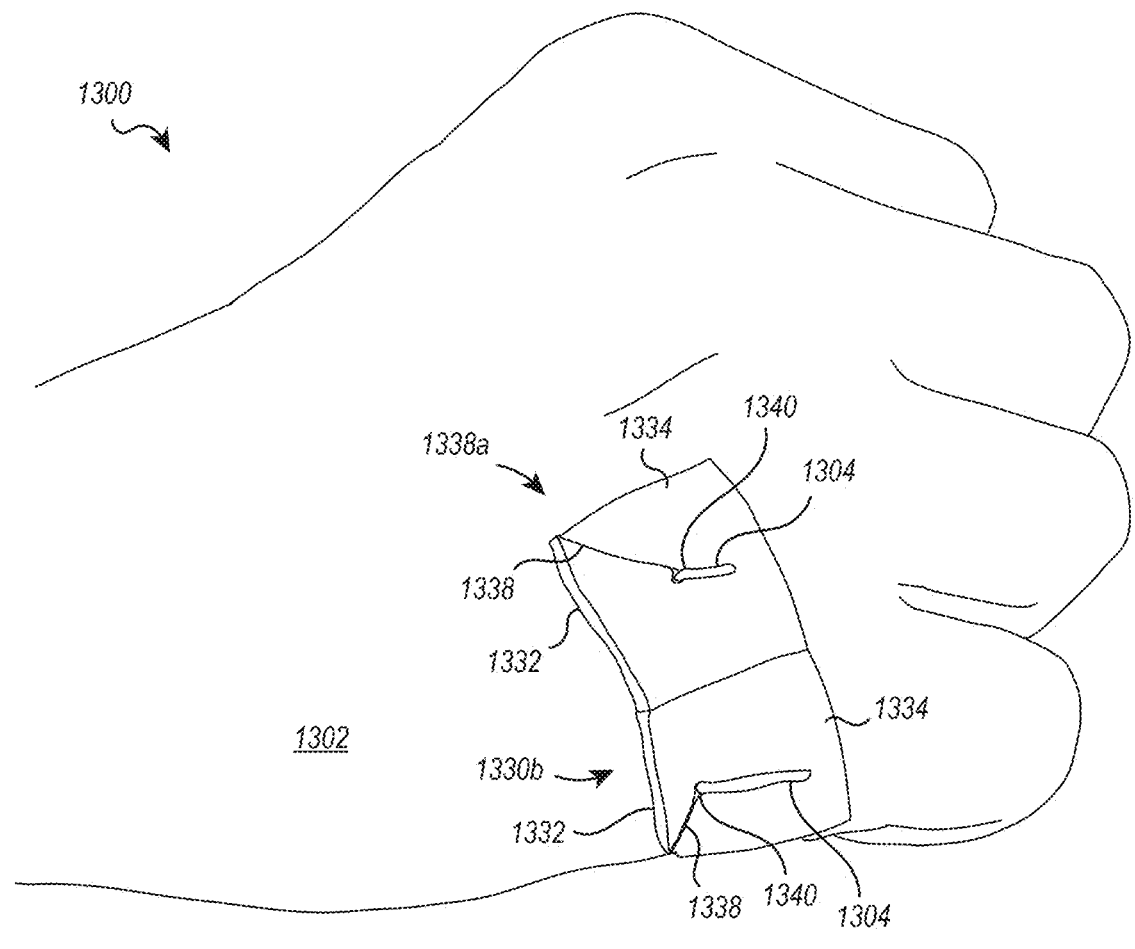
Figure 14:
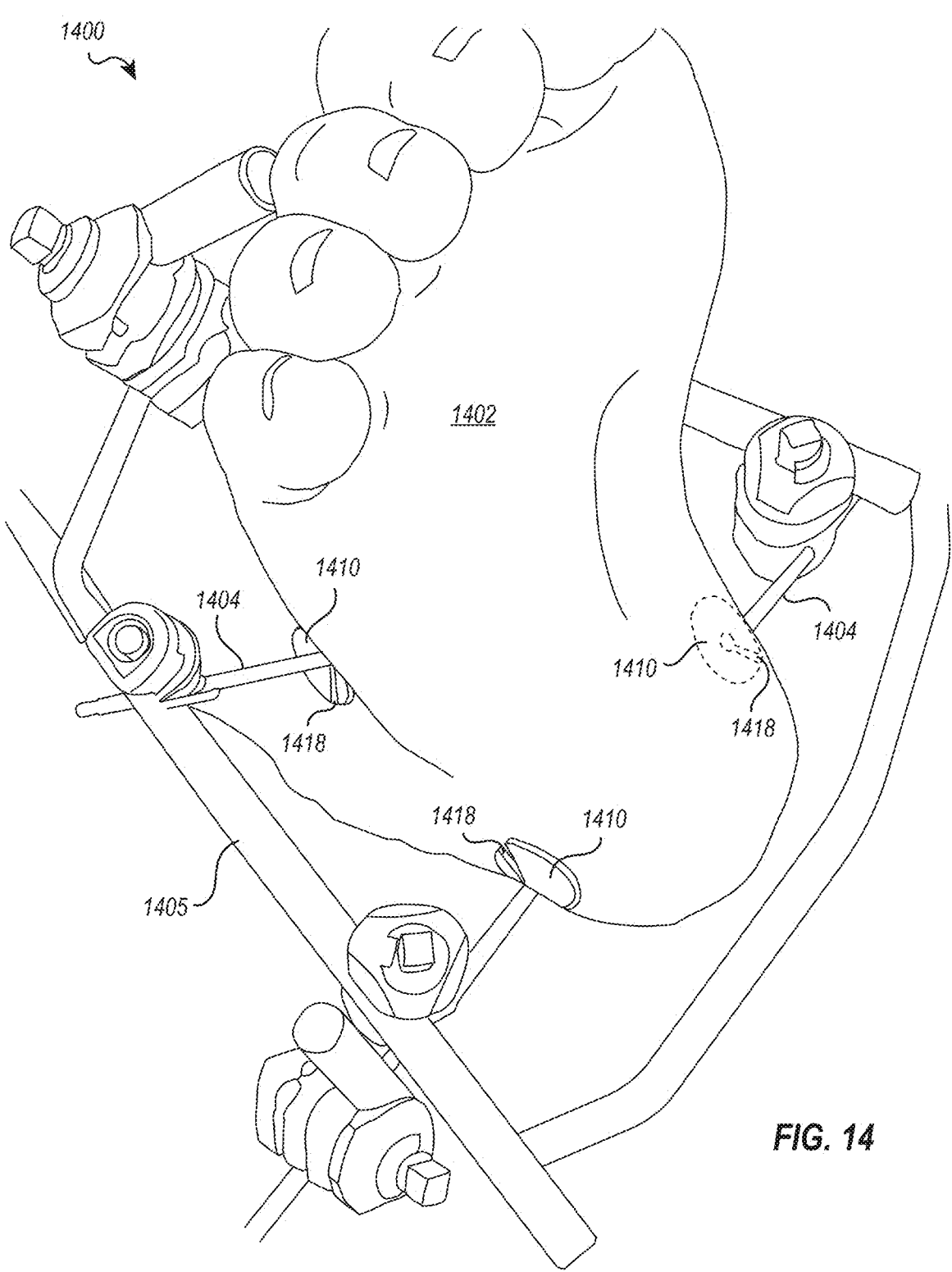
Figure 15:
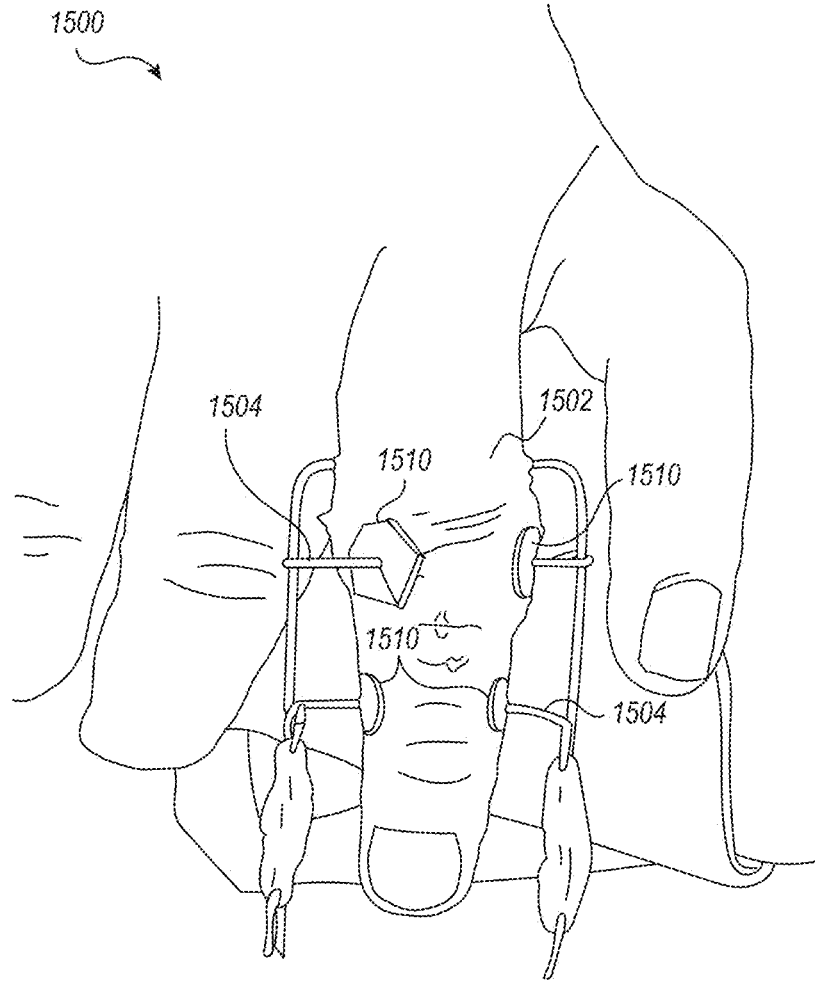

6 antimicrobial barrier at a surgical site with one or more percutaneous pins or wires protruding from the skin;

FIG. 5A is a top perspective view and FIG. 5B is a side cross-sectional view that schematically illustrate a surgical site with a percutaneous pin or wire protruding from the skin and a protective bandage according to the disclosure applied at the surgical site, with the percutaneous pin or wire passing through a slit of the bandage;

FIGS. 6A-6E are schematically illustrate bandages according to the disclosure that have various geometric shapes designed to protect and provide an antimicrobial barrier at a surgical site with one or more percutaneous pins or wires protruding from the skin;

FIG. 7A is a perspective view of a surgical site with a plurality of percutaneous pins or wires protruding from the skin;

FIG. 7B is a perspective view of the surgical site of FIG. 7A with a plurality of bandages applied at the surgical site and with the percutaneous pins or wires extending through respective slits of the bandages;

FIGS. 8A and 8B schematically illustrate embodiments of a bandage having a plurality of slits designed to protect and provide an antimicrobial barrier at a surgical site with a plurality of percutaneous pins or wires protruding from the skin;

FIG. 9 illustrates two bandages with different slit designs to protect and provide an antimicrobial barrier at a surgical site with one or more percutaneous pins or wires protruding from the skin, with one bandage having a narrower slit and the other bandage having a wider slit;

FIG. 10 schematically illustrates two bandage configurations designed to protect and provide antimicrobial activity at a surgical site with one or more percutaneous pins or wires protruding from the skin, with one being a single bandage and the other being a double bandage with one bandage being stacked over the other bandage, and a third bandage with a central opening but no slit for comparison;

FIG. 11 illustrates a surgical site with a hand that has been surgically repaired using two surgical pins or wires that protrude from the skin and bandages with central openings but no slits applied at the surgical site, with the percutaneous pins or wires extending through respective central openings of the bandages;

FIG. 12 illustrates a surgical site with a hand that has been surgically repaired using a surgical pin or wire that protrudes from the skin and a protective bandage according to the disclosure placed at the surgical site, with the percutaneous pin or wire extending through a slit of the bandage;

FIG. 13 illustrates a surgical site with a hand that has been surgically repaired using two surgical pins or wires that protrude from the skin and protective bandages according to the disclosure placed at the surgical site, with the percutaneous pins or wires extending through respective slits of the bandages;

FIG. 14 illustrates a surgical site with a foot that has been surgically repaired using a plurality of percutaneous surgical pins or wires that protrude from the skin and protective bandages according to the disclosure placed at the surgical with the percutaneous pins or wires extending through respective slits of the bandages; and FIG. 15 illustrates a surgical site with a badly crushed finger that has been surgically repaired using a plurality of percutaneous surgical pins or wires that protrude from the skin and protective bandages according to the disclosure placed at the surgical with the percutaneous pins or wires extending through respective slits of the bandages.

DETAILED DESCRIPTION

The present disclosure relates to bandages (e.g., dressings) configured to provide antimicrobial protection, exudate absorption, and mechanical stability at a surgical site with one or more percutaneous pins or wires protruding beyond the skin. The bandage includes an adhesive layer, an absorbent layer, an antimicrobial agent adjacent to and/or impregnated in one or both of the absorbent layer and adhesive layer, and one or more slits through the bandage designed to accommodate and receive therethrough a percutaneous pin or wire. The bandages disclosed herein advantageously enhance and facilitate case of bandaging and providing wound care at a surgical site with one or more percutaneous pins or wires protruding from the skin without disturbing the one or more percutaneous pins or wires.

As used herein, the term "percutaneous pin or wire" broadly refers to any percutaneous pin or wire extending through and out of the skin of a patient, such as surgical pins or wires, orthopedic pins or wires, pins and wires used in plastic surgery, and pins and wires used in ear nose and throat (ENT) procedures. In some embodiments, the "percutaneous pin or wire" may refer to a Kirschner wire (K-wire), external fixation pin, and/or a Steinmann pin.

As used herein, the term "wound care" generally refers to procedures commonly used by medical practitioners and the like to care for an open or surgical wound of a patient. For instance, wound care may include one or more of providing antimicrobial protection, absorbing wound exudate, or providing mechanical stability to one or more percutaneous pins or wires.

Surgical sites with one or more percutaneous pins or wires extending therefrom present a unique challenge to surgeons and other medical practitioners during initial placement, as well as medical practitioners and patients when it is desired to remove an old or dirty bandage and replace it with a fresh bandage during the recovery period following surgery. For instance, percutaneous pins or wires prevent closure of open wounds from which the percutaneous pins or wires extend until the percutaneous pins or wires have been removed (see FIGS. 1 and 2). Therefore, medical practitioners must keep such surgical sites bandaged to prevent excessive fluid leakage from the one or more open wounds and prevent infection or contamination of the one or more open wounds for as long as the percutaneous pins or wires remain at the surgical site. Currently, medical practitioners use makeshift bandages that are not designed for use with percutaneous (e.g., surgical or orthopedic) pins or wires (see FIG. 3).

Figure 1:
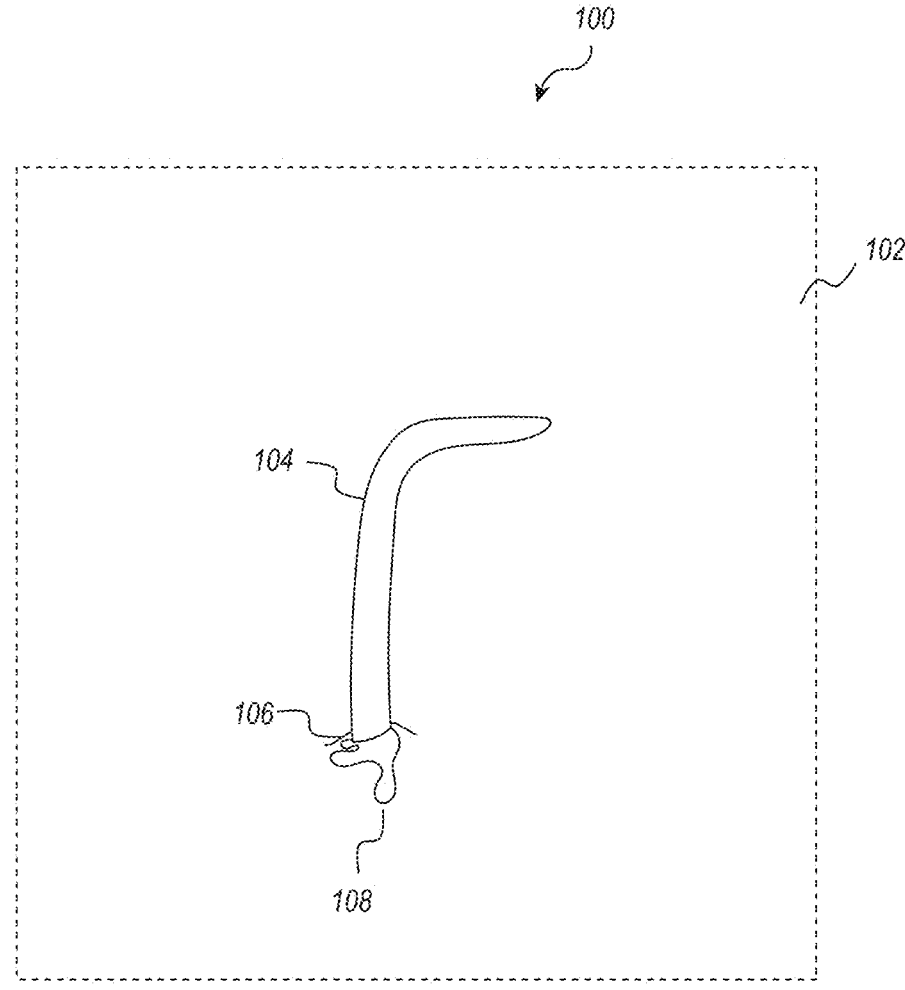
FIG. 1 schematically illustrates a surgical site with a percutaneous pin or wire protruding from the skin.
Figure 2:
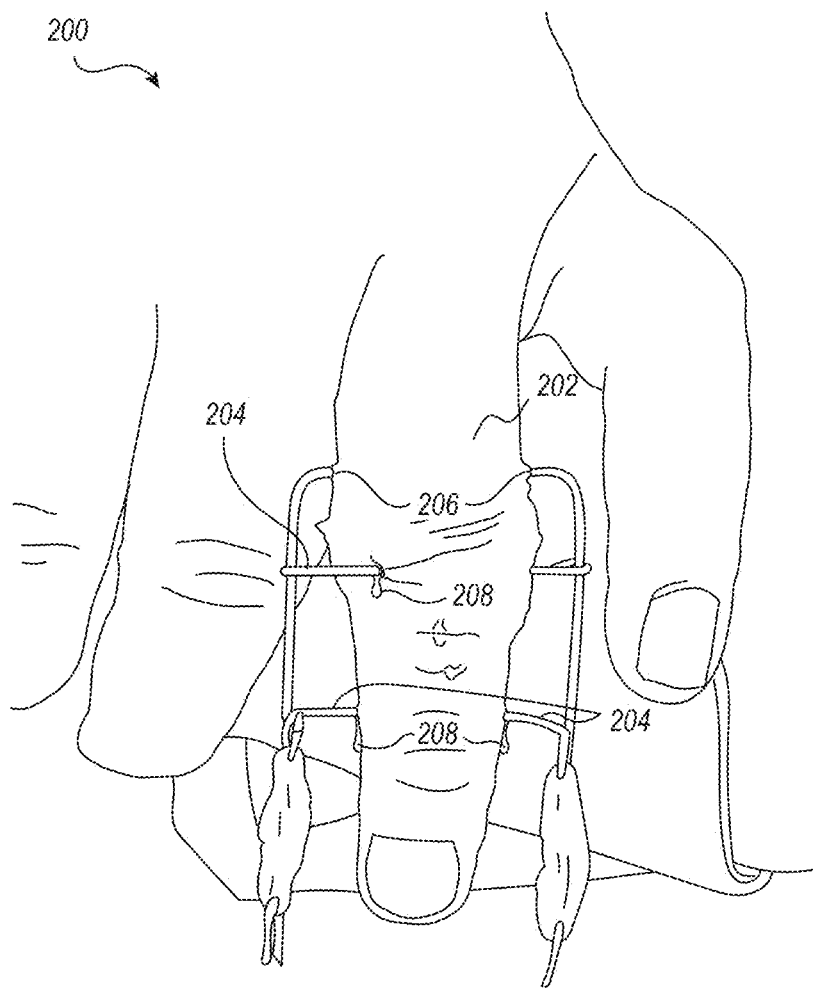
FIG. 2 illustrates a surgical site with a badly crushed finger that has been surgically repaired using a plurality of percutaneous pins or wires that protrude from the skin.
Figure 3:
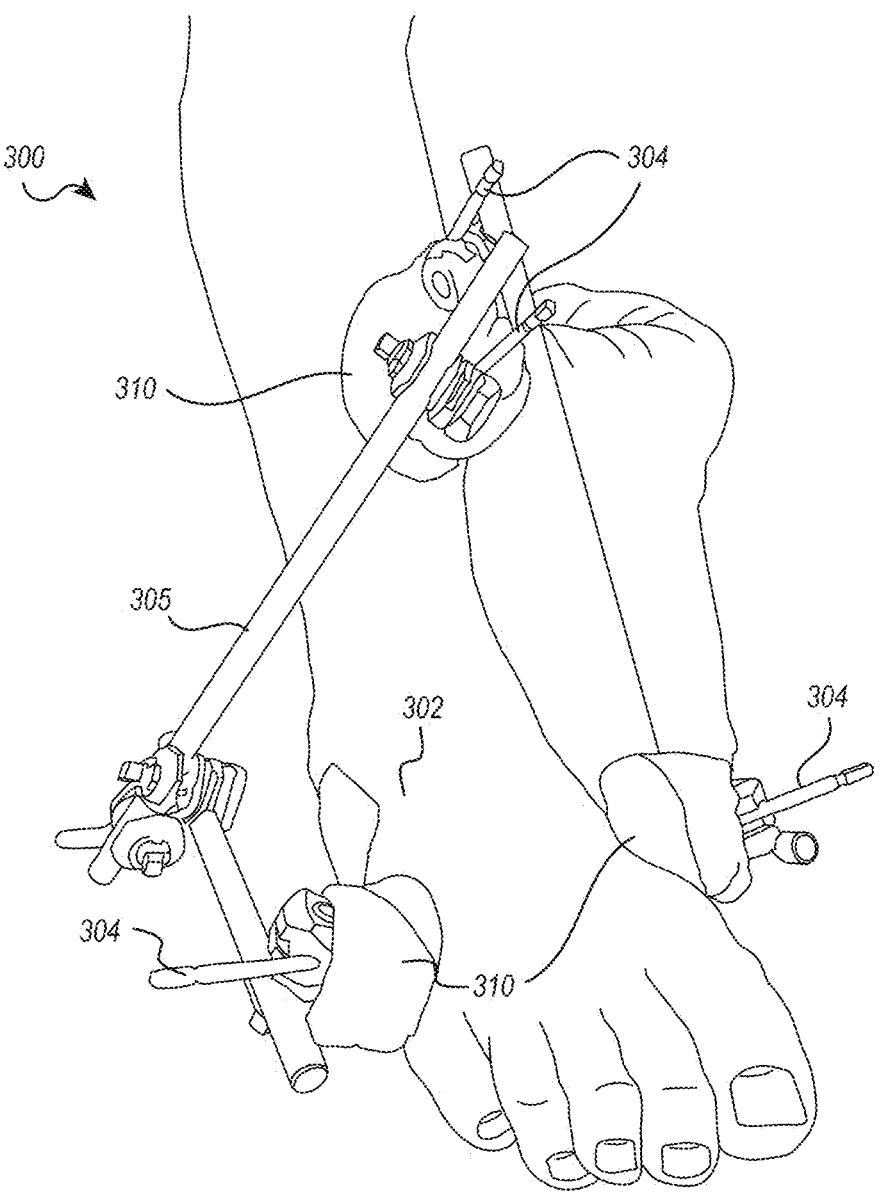
FIG. 3 illustrates a surgical site with a foot that has been surgically repaired using a plurality of percutaneous pins or wires that protrude from the skin and which are covered with makeshift gauze bandages.

Furthermore, percutaneous pins or wires are often bent, modified, or attached to external structures (e.g., as illustrated in FIGS. 1-3) to prevent excessive movement of the pins or wires, such as tearing of the skin or migration of the pins or wires beneath the skin of a patient. For example, percutaneous pins or wires may be bent into a Shepard's crook (illustrated in FIG. 1), may be interconnected together in a cage-like structure (illustrated in FIG. 2), or be fastened to external hardware (illustrate in FIG. 3).

Because surgical sites can have one or more percutaneous pins or wires that have been bent, modified, or attached to an external structure extending therefrom, traditional bandages or dressings used to cover and provide an antimicrobial barrier at a surgical site must be modified, sometimes extensively, in a manner that changes their intended use in order to accommodate percutaneous surgical pins or wires.

Specifically, it is desirable for a bandage or dressing to adhere to and be flush with the skin surface at the surgical site to prevent fluid buildup and prevent contaminants and microbes from breaching the bandage and contaminating or infecting the surgical site.

Thus, traditional bandages must be cut, punctured, combined, secured with tape, or otherwise modified to meet the standard of care required to protect and provide a protective barrier to the surgical site with one or more percutaneous pins or wires extending therefrom. This modification process is not standardized and can be cumbersome or inconsistent, which can extend the amount of time open wounds at a surgical site are exposed to air as well as increase the risk that the percutaneous pins or wires will be disturbed when a modified bandage or dressing is placed and secured at the surgical site.

Furthermore, percutaneous pins or wires often remain in the body of a patient for extended periods of time (from weeks to months) to facilitate bone stabilization and healing. Therefore, patients are often required to periodically clean a surgical site with one or more percutaneous pins outside of a clinical setting. For example, patients may be instructed to clean the surgical site at home and change bandages at the surgical site that includes protruding pins or wires. Because patients typically lack the training or expertise to properly sterilize and dress an open wound, the bandages disclosed herein, which are specifically designed to standardize and simplify the process of providing an antimicrobial barrier and dressing an open wound with percutaneous pins or wires, greatly simplify and standardize the process, thus preventing errors by inexperienced patients or marginally competent medical practitioners.

The bandages disclosed herein overcome at least some of the aforementioned shortcomings of conventional bandages or dressings that must be modified to protect and provide an antimicrobial barrier at a surgical site with one or more percutaneous pins or wires extending therefrom. The disclosed bandages are specifically designed to protect and provide an antimicrobial barrier to surgical sites that include one or more percutaneous pins or wires. To facilitate case of use by medical practitioners and patients, the disclosed bandages advantageously include an antimicrobial agent, an absorbent layer, an adhesive layer, and one or more slits designed to accommodate and receive therethrough, and circumferentially close or seal around, a percutaneous pin or wire.

The adhesive layer is advantageously configured to reliably adhere to tissue at the surgical site and prevent dislodgement of the bandage during its intended use. The adhesive layer facilitates easy attachment and removal of the bandage to and from the surgical site without further modification or application of tape. The adhesive layer is also advantageously configured so that the bandage can be removed from the surgical site without significantly damaging tissue. For instance, the adhesive layer may prevent discomfort and/or trauma to the surgical site as the bandage is removed from the surgical site. This is in contrast to conventional tape, which can adhere more strongly to skin and other tissue and cause damage thereto when removed, particularly when the skin or other tissue is still weak and tender following surgery.

The absorbent layer is advantageously a porous and/or hydrophilic substance configured to absorb wound exudate (e.g., blood, blood components, plasma, serum, and/or serosanguineous discharges) that may leak from one or more open wounds, such as those caused by the percutaneous (e.g., surgical and orthopedic) pins or wires. The absorbent layer is configured to absorb and contain wound exudate from, and facilitate healing of, the one or more open wounds. The absorbent layer reduces or minimizes further leakage from the one or more wounds and increases the anti-infection properties of the bandage. Furthermore, the absorbent layer protects the skin from symptomatic pin or wire migration, thereby providing mechanical stabilization to the one or more percutaneous pins or wires.

The antimicrobial agent is advantageously provided within the absorbent layer, the adhesive layer, both the absorbent layer and the adhesive layer, and/or as separate antimicrobial layer (e.g., between the adhesive and absorbent layers), wherein the antimicrobial agent provides antimicrobial protection to a surgical site (e.g., disinfects and/or maintains sterility) when a bandage is placed thereon. The antimicrobial agent thus prevents complications related to infection of the one or more open wounds from which one or more percutaneous pins or wires extend.

The slit is a pre-cut opening across a portion of the width or diameter of the bandage and is tailored to receive and fit snugly around the percutaneous surgical pin or wire. When properly placed, the slit facilitates placement of the bandage circumferentially around the pin or wire in order to provide a reliable physical barrier to prevent ingress of contaminants at the surgical site, particularly at the wound provided by the protruding pin or wire. A properly placed bandage not only provides a reliable barrier to maintain sterility of the surgical site, it can also provide structural immobilization of the percutaneous pin or wire that minimizes movement of, or potential irritation caused by movement of, the percutaneous pin or wire. Furthermore, the slit facilitates placement of the bandage over and around a percutaneous pin or wire without disturbing it and without compromising the protective and antimicrobial properties of the bandage.

In some embodiments, the bandage further comprises a pre-cut central opening in communication with the slit, wherein the central opening is tailored to fit snugly around a percutaneous pin or wire, thereby facilitating proper placement of the bandage and potentially improving the seal around the pin or wire.

In preferred embodiments, the materials used to form the bandage are flexible, allowing for the bandage to conform to the contours of surgical sites at any location on the body of a patient. The flexible materials can facilitate manipulation of the bandage in order to maximize adherence to and sealing of tissue and pin or wire. Furthermore, flexible materials can accommodate movement or shifting of the percutaneous pins or wires without dislodging or tearing.

Figure 4A:
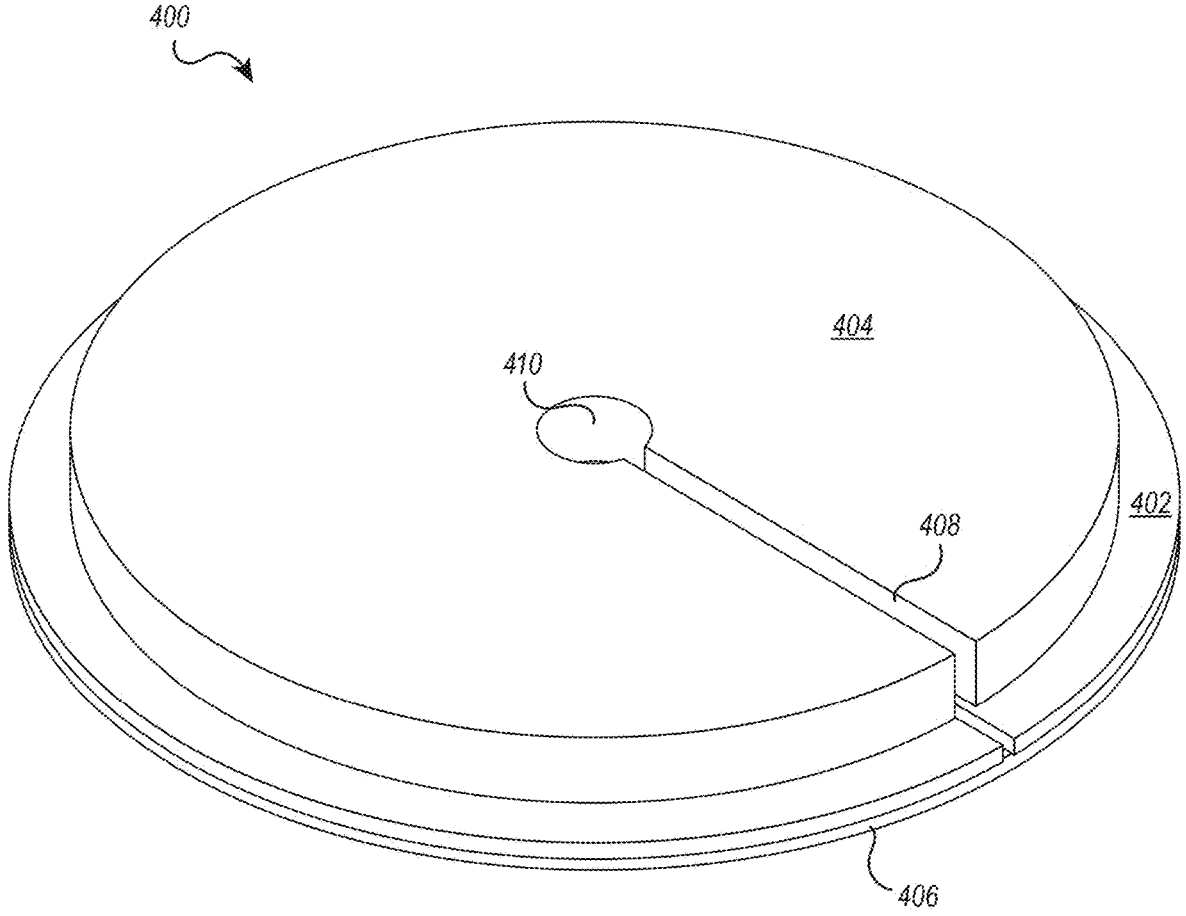
Figure 4B:
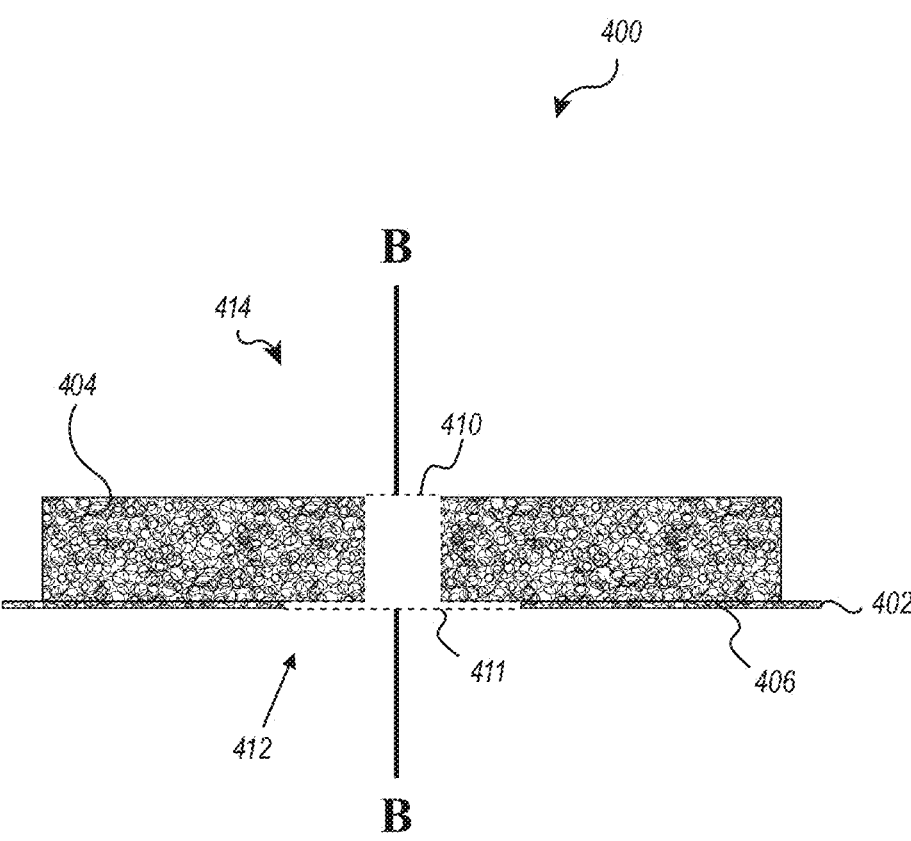

Turning now to the drawings, FIGS. 4A and 4B illustrate a first embodiment of a protective bandage 400 according to the disclosure for use in protecting and disinfecting to a surgical site with one or more percutaneous pins or wires. The bandage 400 includes an adhesive layer 402, which includes a first side configured to adhere to tissue and a second side opposite the first side, and an absorbent layer 404 adhered to the second side of the adhesive layer 402. A protective film or backing layer 406 initially covers the first side of the adhesive layer 402 to maintain the cleanliness and adhesive properties of the adhesive layer 402 during storage and prior to use. The protective film 406 can be removed from the adhesive layer 402 prior to use to expose the first side and permit it to adhere to tissue at a surgical site. As shown in FIG. 4B, the bandage 400 has a proximal side 412 oriented toward tissue during use and a distal side 414 opposite the proximal side 412.

The bandage 400 further includes a slit 408 extending partially across the width or diameter of the bandage 400 and a central opening 410 through the absorbent layer and a larger opening 411 through the adhesive layer. The slit 408 and central opening 410 facilitate placement of the bandage 400 at a surgical site and are configured to receive a surgical pin or wire (not shown) during placement of the bandage at a surgical site. The slit 408 permits the bandage 400 to be moved laterally relative to a surgical pin or wire protruding from the surgical site, so as to not disturb or put undue force on the percutaneous pin or wire. The central opening 410 is designed to surround and form a seal against an outer perimeter of the percutaneous pin or wire when the bandage 400 is placed at a surgical site. The central opening may be in the center of the bandage or may be offset depending on the length of the slit (e.g., it can be off center to match the length of the slit relative to the diameter or width of the bandage). In other embodiments, the central opening 410 can be omitted, with the flexibility of the bandage and absorbent layer being sufficient to conform to and seal around the percutaneous pin or wire.

The larger opening 411 through the adhesive layer 402 permits the absorbent layer 404 to contact the surgical site to facilitate absorption of wound exudate and provide antimicrobial activity (e.g., where the absorbent layer 404 includes an antimicrobial agent impregnated therein. Alternatively, in the case where a separate antimicrobial layer (not shown) is positioned between the adhesive layer 402 and the absorbent layer 404, the larger opening 411 permits direct contact of the antimicrobial layer to tissue at the surgical site. The larger opening may have any desired size and can have a diameter that is between about 10-90%, or about 20-80%, or about 30-70%, or about 40-60%, of the width or diameter of the bandage.

As illustrated in FIG. 4B, the adhesive layer 402, absorbent layer 404, and backing layer 406 of the bandage 100 are axially aligned along a vertical axis B-B. As best seen in FIG. 4A, the slit 408 extends through the adhesive layer 402 and absorbent layer 404. The slit 408 can be formed by a first slit portion in the adhesive layer 402 and a second slit portion in the absorbent layer 404. The first slit and the second slit are advantageously axially aligned along vertical axis B-B such that they form the slit 408. It will be appreciated that the first and second slits can have the same or different widths depending on the intended use or functionality of the bandage 400. In some embodiments, an adhesive material may be disposed on at least a portion of the inside walls of slit 408 so that, when pressed together, slit 408 can be adhesively closed and form a physical barrier to microbes and dirt as if there were no slit 408.

The slit 408 is designed to accommodate a surgical wire or a percutaneous pin passing therethrough, wherein the protruding portion of the wire or pin may extend through the entirety of the bandage 400 via the slit 408. In various embodiments, the slit 408 can have a width that is the same as, similar to, or smaller than the diameter of the percutaneous pin or wire extending therethrough to reduce the amount of the surgical site exposed to open air. Accordingly, the slit 408 can have a width in a range from about 0.4 mm to about 10 mm, such as from about 1 mm to about 7.5 mm, or from about 1.5 mm to about 5 mm, or from about 0.45 mm to about 0.62 mm, or from about 0.7 mm to about 1.5 mm, or from about 1.5 mm to about 6.5 mm, or from about 4 mm to about 4.5 mm, or from about 5.5 mm to about 6.5 mm, or within a range bounded by any two of the foregoing.

In some embodiments, the slit 408 may have a length that extends across at least a portion of the diameter (or width, depending on the shape) of the bandage 400. For instance, the slit may have a length that extends across about 20% to about 80% of the diameter or width of the bandage, or about 30% to about 70% of the diameter or width of the bandage, or about 40% to about 60% of the diameter or width of the bandage, or about 45% to about 55% of the diameter or width of the bandage.

In some embodiments, a central opening 410 extends through the axially aligned layers of the bandage 400, wherein the central opening 410 extends through the proximal side 412 and the distal side 414 along a vertical axis B-B. As shown in FIG. 4B, the central opening 410 is formed in the absorbent layer 404, with a larger opening 411 formed in the adhesive layer 404. The central opening 410 and the larger opening 411 can be axially aligned along vertical axis B-B such that they form essentially concentric openings 410, 411. It will be appreciated that the openings 410, 411 can be non-concentric depending on the intended use or functionality of the bandage 400. The central opening 410 is in communication with the slit 408, such that the central opening 410 and slit 408 form a slit/opening complex configured to accommodate and fit snugly around a percutaneous pin or wire passing therethrough.

In embodiments that include the central opening 410, the central opening 410 is designed to accommodate a percutaneous wire or a surgical pin passing therethrough, wherein the percutaneous wire or pin may extend through the entirety of the bandage 400 via the central opening 410. In various embodiments, the central opening 410 can have a diameter that is the same as, similar to, or smaller than the diameter of the percutaneous wire or pin extending therethrough to reduce the amount of the surgical site exposed to open air. Accordingly, the central opening 410 can have a diameter in a range of about 0.4 mm to about 10 mm, such as about 1 mm to about 7.5 mm, or about 1.5 mm to about 5 mm, or about 0.45 mm to about 0.62 mm, or about 0.7 mm to about 1.5 mm, or about 1.5 mm to about 6.5 mm, or about 4 mm to about 4.5 mm, or about 5.5 mm to about 6.5 mm.

In some embodiments, as illustrated in FIG. 4B, the central opening 410 is positioned in the center of the bandage 400. However, it is appreciated that the central opening 410 may be off center, such as where it is desired for a portion of the bandage to extend further in one direction than another relative to the percutaneous pin or wire.

The adhesive layer 402, absorbent layer 404, and/or an antimicrobial layer (not pictured) can include (i.e., be impregnated with) an antimicrobial agent. Examples of antimicrobial agents include, but are not limited to, one or more of silver (e.g., silver nanoparticles and silver salts, such as silver nitrate and silver sulfadiazine, ionic silver, and nanocrystalline silver), iodine (e.g., povidone iodine and cadexomer iodine), chlorhexidine (e.g., chlorhexidine gluconate), polyhexamethylene biguanide (PHMB), honey, antibiotics (e.g., gentamicin, mupirocin, and bacitracin), hypochlorous acid, gentian violet, and essential oils (e.g., tea tree oil), and/or other substances capable of providing an antimicrobial barrier or other antimicrobial activity to a surgical site or wound.

The absorbent layer 404 can be formed from a hydrophilic material capable of absorbing fluid leakage from a wound site. Examples of hydrophilic materials include, but are not limited to, silicone, cotton wool, gauze, lint, plasters, foam, alginate, hydrocolloid, hydrogel, and or others capable of absorbing fluid leakage from a surgical or other wound site. In some embodiments, the absorbent layer 102 may be impregnated with a hemostatic agent, examples of which include one or more of thrombin, thrombin enzyme, prothrombin complex concentrate, dried plasma, cyanoacrylate, fibrin sealant, tranexamic acid, microfibrillar collagen, microporous polysaccharide spheres, gelatin matrix, oxidized regenerated cellulose, alginate, albumin, glutaraldehyde, alum (hydrated salts of aluminum and alkali metals), aluminum chloride, zinc chloride, ferric sulfates, and/or others capable of reducing bleeding or other fluid leakage from a surgical or other wound site.

The adhesive layer 402 forms the proximal side 412 of the bandage 400, wherein the adhesive layer 402 is configured to contact tissue at the surgical site. In some instances, the absorbent layer 404 may extend through one or more portions of the adhesive layer 402 (e.g., through larger opening 411) such that part of the absorbent layer 404 may be exposed at the distal side 414 to improve the absorbent and/or antimicrobial properties of the bandage 400. For instance, the absorbent layer 404 may cover from about 0% to about 90%, or from about 25% to about 75%, or from about 40% to about 60%, of the of the surface area of the distal side 414.

The adhesive layer 402 can be formed from or include an adhesive material configured to attach bandage 400 to tissue at a surgical site, examples of which include, but are not limited to, hydrocolloids, acrylic polymer films, cyanoacrylate films, silicone films, and/or other materials capable of attaching to skin at a surgical site. In some embodiments, the adhesive layer 402 is formed from a gel-like or malleable substance (e.g., hydrocolloid) such that the adhesive layer 402 can make good contact with and adhere to tissue around a percutaneous pin or wire passing through the slit 408 and/or central opening 410. In some embodiments, the adhesive layer 402 includes a protective film 406 (e.g., backing layer) that may be removed from the adhesive layer 402 prior to use. The protective film 406 maintains the cleanliness and adhesive properties of the adhesive layer 402 during storage and prior to use.

In some embodiments, the adhesive layer 402 can be impregnated with an antimicrobial agent, such that the adhesive layer 402 provides easy attachment of bandage 400 to tissue as well as provide antimicrobial protection to a wound.

The individual layers and/or combined layers form the bandage 400, wherein the bandage 400 has a height or cross-sectional thickness taken along the vertical axis B-B in a range of about 0.1 cm to about 10 cm, about 0.2 cm to about 8 cm, about 0.5 cm to about 5 cm, or about 0.75 cm to about 3 cm. The adhesive layer 402 may have a relatively small cross-sectional thickness, such as about 0.1 mm to about 2 mm, or about 0.2 mm to about 1.5 mm, or about 0.3 mm to about 1 mm, with the majority of the height or cross-sectional thickness of the bandage 400 comprising or being provided by the absorbent layer 404. Furthermore, the bandage 400 may have a diameter or width in a range from about 0.5 cm to about 12 cm, or about 0.75 cm to about 10 cm, or about 1 cm to about 8 cm, or about 1.5 cm to about 6 cm, or about 2 cm to about 5 cm. The foregoing ranges are applicable to the other embodiments disclosed herein.

FIGS. 5A and 5B illustrate a bandage 500 applied to a surgical site 501, wherein the percutaneous pin/wire 505 is received through a slot 508 and central opening 510. The adhesive layer 502 is placed on the skin surface 503, attaching the bandage 500 to the surgical site 501 without modification, which is a substantial improvement over makeshift or ad hoc dressings currently used, such as wrapping with gauze, securing with tape, or other methods of securing a bandage to a surgical site. As illustrated in FIGS. 5A and 5B, the bandage 500 provides a barrier between the wound (covered by bandage 500), which is formed by the percutaneous pin or wire 505 penetrating through and protruding from the skin 503, and open air, provides antimicrobial protection by the antimicrobial agent, and absorbs wound exudate (covered by bandage 500) by the absorbent layer 504.

The bandage 500 and other bandages disclosed herein can be used to improve wound care, increase the case of bandaging various surgical sites, such as those illustrated in FIGS. 1-3 and further illustrated in FIGS. 12-16, and improve patient outcomes by standardizing the process of bandaging a surgical site with one or mor percutaneous pins or wires.

In some embodiments, bandages disclosed herein may have a desired geometric shape. For instance, bandages may be circular, as illustrated in FIGS. 4A-4B and 5A-5B. Alternatively, such as those illustrated in FIGS. 6A-6E, bandages 600 may be square, rectangular, hexagonal, pentagonal, triangular, octagonal, or another geometric shape that allows the application of multiple adjacent bandages 600 to attach to and protect a surgical site with one or more percutaneous pins or wires extending therefrom. The shape of the bandage 600 may assist a medical practitioner in covering or substantially covering a skin surface at a surgical site comprising more than one percutaneous pin or wire to form a continuous and uninterrupted barrier to prevent contamination and infection. The bandages 600 illustrated in FIGS. 6A-6E are shown bottom side up, with the backing layer 606 at the top.

FIG. 6A illustrates a square-shaped bandage 600*a* having an adhesive layer 602, an absorbent layer 604, a backing layer on the proximal side of adhesive layer 602, a slit 608 passing partially through the bandage 600*a*, a pin or wire opening 610 through the absorbent layer 604, and a larger opening 611 through the adhesive layer 602 so that a portion of the absorbent layer 604 and associated antimicrobial agent can contact skin at a surgical site. Although the slit 608 is shown extending from a corner of the square-shaped bandage 600*a* to the opening 610, it will be appreciated that it may extend from a side of the bandage 600*a* to the opening 610.

FIG. 6B illustrates a hexagonal-shaped bandage 600*b* having an adhesive layer 602, an absorbent layer 604, a backing layer on the proximal side of adhesive layer 602, a slit 608 passing partially through the bandage 600*b*, a pin or wire opening 610 through the absorbent layer 604, and a larger opening 611 through the adhesive layer 602 so that a portion of the absorbent layer 604 and associated antimicrobial agent can contact skin at a surgical site. Although the slit 608 is shown extending from a corner of the hexagonal-shaped bandage 600*b* to the opening 610, it will be appreciated that it may extend from a side of the bandage 600*b* to the opening 610.

FIG. 6C illustrates a pentagonal-shaped bandage 600*c* having an adhesive layer 602, an absorbent layer 604, a backing layer on the proximal side of adhesive layer 602, a slit 608 passing partially through the bandage 600*c*, a pin or wire opening 610 through the absorbent layer 604, and a larger opening 611 through the adhesive layer 602 so that a portion of the absorbent layer 604 and associated antimicrobial agent can contact skin at a surgical site. Although the slit 608 is shown extending from a corner of the pentagonal-shaped bandage 600*c* to the opening 610, it will be appreciated that it may extend from a side of the bandage 600*c* to the opening 610.

FIG. 6D illustrates a triangular bandage 600*d* having an adhesive layer 602, an absorbent layer 604, a backing layer on the proximal side of adhesive layer 602, a slit 608 passing partially through the bandage 600*d*, a pin or wire opening 610 through the absorbent layer 604, and a larger opening 611 through the adhesive layer 602 so that a portion of the absorbent layer 604 and associated antimicrobial agent can contact skin at a surgical site. Although the slit 608 is shown extending from a corner of the triangular bandage 600*d* to the opening 610, it will be appreciated that it may extend from a side of the 600*d* to the opening 610.

Figure 6E:
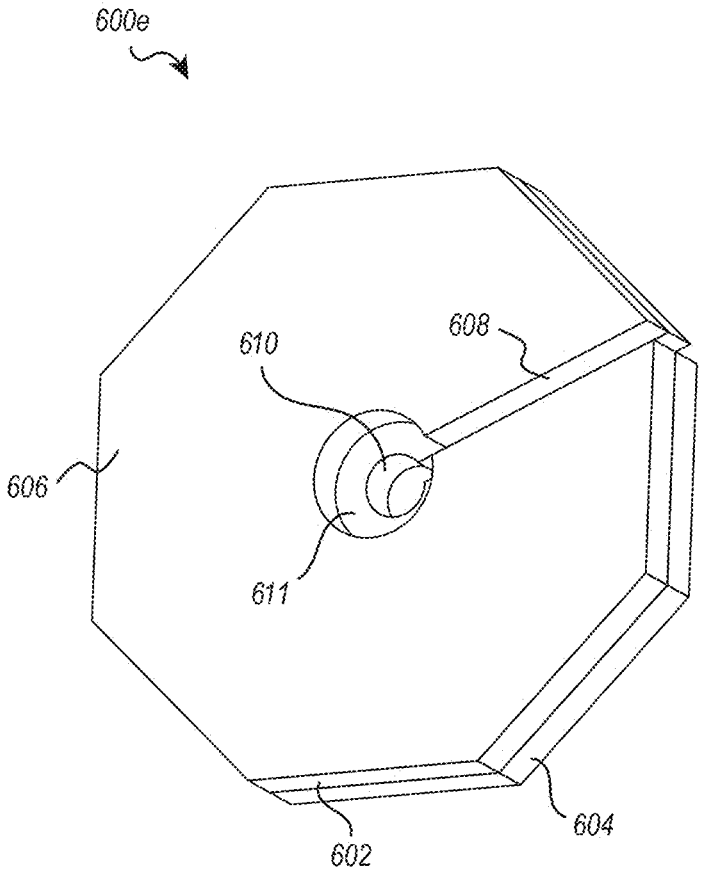

FIG. 6E illustrates an octagonal-shaped bandage 600*e* having an adhesive layer 602, an absorbent layer 604, a backing layer on the proximal side of adhesive layer 602, a slit 608 passing partially through the bandage 600*e*, a pin or wire opening 610 through the absorbent layer 604, and a larger opening 611 through the adhesive layer 602 so that a portion of the absorbent layer 604 and associated antimicrobial agent can contact skin at a surgical site. Although the slit 608 is shown extending from a corner of the octagonal-shaped bandage 600*e* to the opening 610, it will be appreciated that it may extend from a side of the bandage 600*e* to the opening 610.

By way of example, FIGS. 7A and 7B illustrate how multiple bandages 700 of various geometric shapes and sizes can be combined to form a bandaging system to more fully cover, protect, and provide antimicrobial activity at a large region of a surgical site. FIG. 7A illustrates a surgical site 720 comprising skin surface 722, wherein three percutaneous pins/wires 724 extend therefrom, leaving wounds 726 exposed at the skin surface 722 and permitting leakage of fluid or exudate 728 from the wounds 726.

FIG. 7B illustrates an arrangement of multiple bandages 700 disposed at the surgical site 720. The multiple bandages 700 comprise different shapes that can be selected to fit together and form a bandage system that comprehensively covers the surgical site 720 without significant gaps and/or overlap. As illustrated, the bandage system includes two octagonal-shaped bandages 700*a*, 700*b* that abut each other, a hexagonal-shaped bandage 700*c* that abuts bandage 700*a*, and a square-shaped bandage 700*d* that abuts each of bandages 700*a*, 700*b*, 700*c* to fill in a gap between bandages 700*b*, 700*c*. As illustrated, one or more bandages 700 can be used to cover a portion of the skin surface 722 without being placed around a percutaneous pin or wire 724 (i.e., the squares-shaped bandage 700*d*).

In some instances, a patient may be instructed to clean and re-dress their surgical recovery site with one or more percutaneous pins or wires outside of a clinical setting. In such instances, patients without medical training would be expected to re-dress such a surgical recovery site aseptically and without disturbing the one or more percutaneous pins or wires. A bandage or a kit of bandages as disclosed herein may be prescribed to a patient in order to facilitate easy unbandaging and rebandaging of the recovery site. A kit of bandages may be particularly useful when a patient is required to replace bandages at a recovery site with a plurality of percutaneous pins or wires. For example, a kit may provide a patient with multiple sets of correctly-sized and shaped bandages used to comprehensively cover the recovery site and accommodate the percutaneous wires or pins. The kit may additionally include wound cleaning supplies, instructions for correct application of the bandages, and/or other information regarding at-home care.

By way of example, a kit may comprise one or more sets of the bandages as illustrated in FIG. 7B, instructions on where to place each bandage at the surgical recovery site, and instructions on how often to change the bandages. The instructions may include written instructions and/or a schematic of the wound site (such as the schematic illustration presented in FIG. 7B).

FIG. 8A illustrates another embodiment of a bandage 800, which comprises an adhesive layer 802, an absorbent layer 804, and a plurality (e.g., two) of slits 808 to accommodate and receive therethrough a plurality of (e.g., two) percutaneous pins or wires extending from a surgical site. The plurality of slits 808 are formed through an axis across the diameter of the bandage 800 so as to be axially aligned. Alternatively, the slits 808 may have other orientations to permit different angles of percutaneous pin or wire insertion. Each slit 808 can be used to accommodate one or more percutaneous pins or surgical wires using a single bandage. The bandage 800 may optionally include pin or wire openings 810, which are illustrated as dotted lines in FIG. 8A, in communication with respective slits 808. In some instances, each slit 808 of the plurality of slits 808 may include an adhesive disposed on a portion of the inside walls of each slit 808, wherein if pressed together, the walls can be adhesively connected to form a continuous barrier.

FIG. 8B illustrates another embodiment of a bandage 800, which comprises an adhesive layer 802, an absorbent layer 804, and a plurality (e.g., two) of slits 808 to accommodate and receive therethrough a plurality of (e.g., two) of percutaneous pins or wires extending from a surgical site. The plurality of slits 808 are formed through an axis across the diameter of the bandage 800 so as to be axially aligned. Alternatively, the slits 808 may have other orientations to permit different angles of pin or wire insertion. Each slit 808 can be used to accommodate one or more percutaneous pins or surgical wires using a single bandage. The bandage 800 may optionally include pin or wire openings 810, which are illustrated as dotted lines in FIG. 8B, in communication with respective slits 808. Furthermore, bandage 800 may include one or more perforations 811 that extend through the thickness of the bandage 800, such that the perforations 811 allow a medical practitioner to open one or more additional slits into the bandage 800.

FIG. 9 illustrates two bandages 900 with different slit designs to protect and sterilize a surgical site with one or more percutaneous pins or wires protruding from the skin, with one bandage having a narrower slit and the other bandage having a wider slit. A first bandage 900a includes a relatively narrow slit 908a with essentially parallel side walls and a central opening 910a. A second bandage 900b includes a wider slit 908b with diverging side walls and a central opening 910b, which can be the same or different diameter as central opening 910a. An advantage of first bandage 900a is the slit is narrow and easy to close together in order to cover and protect skin and wound at a surgical site with one or more percutaneous pins or wires. An advantage of second bandage 900b is the slit is wider at its opening making it easier to slide a percutaneous pin or wire through. The second bandage can be flexible to permit a practitioner to manually close the slit when placing the bandage against the skin. Alternatively, the slit may naturally close together if the bandage is placed in a concave region at a surgical site.

FIG. 10 schematically illustrates two bandage configurations designed to protect and provide antimicrobial activity at a surgical site with one or more percutaneous pins or wires protruding from the skin, and a third bandage with a central opening but no slit for comparison. A first bandage configuration comprises a single bandage 1000 having a slit 1008 and wire or pin opening 1010. A second bandage configuration comprises a first bandage 1000a for application to skin at a surgical site and a second bandage 1000b placed over the first bandage 1000a, each having a slit 1008 and wire or pin opening 1010 which are advantageously aligned. The second bandage configuration can be constructed before placement at the surgical site, or it may be constructed by placing the first bandage 1000a at the surgical site and then placing the second bandage 1000a over the first bandage 1000a.

The third bandage 1020 is a conventional dressing for placement of a catheter therethrough. The third bandage 1020 has a central hole 1022 that is sized to loosely accommodate the diameter of a catheter. However, third bandage 1020 has no adhesive layer or backing layer and is not able to adhere to skin or other tissue in order to stabilize and protect a surgical site with one or more percutaneous pins or wires protruding from the skin. The third bandage 1020 is also of relatively small diameter since its only function is to receive a catheter therethrough attached to a port, not protect the skin at a surgical site.

FIG. 11 illustrates a surgical site 1100 with a hand that has been surgically repaired using two percutaneous pins or wires 1104 that protrude from the skin 1102. A pair of bandages 1120 with central holes but no slits or adhesive are applied at the surgical site of the hand, with the percutaneous pins or wires 1104 extending through respective central holes of the bandages 1120. Because the bandages 1120 lack an adhesive layer, they are unable to adhere to the skin 1102 at the surgical site and provide a reliable antimicrobial barrier. In addition, because the central holes are much larger than the pins or wires 1104, the bandages 1120 are unable to absorb and stop the flow of exudate 1108 and provide a reliable antimicrobial barrier.

FIG. 12 illustrates a surgical site 1200 with a hand that has been surgically repaired using a percutaneous surgical pin or wire 1204 that protrudes from the skin 1202. A protective bandage 1230 according to the disclosure is placed at the surgical site, with the pin or wire 1204 extending through a slit 1338 of the bandage 1230. The bandage 1230 includes an adhesive layer 1232 that reliably adheres the bandage 1230 to the skin 1202 and an absorbent layer 1234 that includes an antimicrobial agent and is configured to absorb any exudate (not shown) that may flow from the wound at the interface of the skin 1202 and wire or pin 1204.

FIG. 13 illustrates a surgical site 1300 with a hand that has been surgically repaired using two percutaneous pins or wires 1304 that protrude from the skin 1302. Two square-shaped protective bandages 1330a, 1330b according to the disclosure are placed adjacent to each other at the surgical site, with the pins or wires 1304 extending through respective slits 1338 of the bandages 1330a, 1330b. The bandages 1330a, 1330b each include an adhesive layer 1332 that reliably adheres the bandages 1330a, 1330b to the skin 1302 and an absorbent layer 1334 that includes an antimicrobial agent and is configured to absorb any exudate (not shown) that may flow from the wound at the interface of the skin 1302 and wires or pins 1304. Abutment of the protective bandages 1330a, 1330b provides a continuous protective layer at the surgical with no gaps therebetween.

FIG. 14 illustrates a surgical site 1400 with a foot that has been surgically repaired using a plurality of percutaneous pins or wires 1404 that protrude from the skin 1402. The pins or wires 1404 are attached to an external stabilization structure 1405, which can complicate placement of bandages as discussed above relative to FIG. 3. Protective bandages 1410 according to the disclosure are placed at the surgical site 1400 with the pins or wires 1404 extending through respective slits 1408 of the bandages 1410. The bandages 1410 each include an adhesive layer that reliably adheres the bandages 1410 to the skin 1402 and an absorbent layer that includes an antimicrobial agent and is configured to absorb any exudate (not shown) that may flow from the wound at the interface of the skin 1402 and wires or pins 1404.

For the sake of comparison, FIG. 14 shows how bandages 1410 according to the disclosure are much smaller and provide a bandage system that is much simpler to apply and replace compared to the bulky makeshift gauze wrap 310 dressings used in FIG. 3, which shows the same surgically repaired foot, percutaneous pins, and external stabilization structure.

FIG. 15 illustrates a surgical site 1500 with a badly damaged finger that has been surgically repaired using a plurality of percutaneous pins or wires 1504 that protrude from the skin 1502. The percutaneous pins or wires 1504 are interconnected in a cage-like structure, which can complicate placement of bandages as discussed above relative to FIG. 2. Protective bandages 1510 according to the disclosure are placed at the surgical site 1500 with the percutaneous pins or wires 1504 extending through respective slits of the bandages 1510. The bandages 1510 each include an adhesive layer that reliably adheres the bandages 1510 to the skin 1502 and an absorbent layer that includes an antimicrobial agent and is configured to absorb any exudate (not shown) that may flow from the wound at the interface of the skin 1502 and the percutaneous wires or pins 1504.

A method for protecting and providing antimicrobial activity (e.g., provide an antimicrobial barrier) at a surgical site with one or more percutaneous pins or wires involves providing a bandage comprising an adhesive layer, an absorbent layer, and an antimicrobial agent forming a separate layer and/or impregnated within one or both of the adhesive layer and absorbent layer, wherein one or more slits extend through the adhesive layer and the absorbent layer. For example, one or more of the various embodiments of bandage, as described hereinabove, may be provided. The method further involves removing a protective film (i.e., a backing layer) from a proximal face of the adhesive layer and placing the adhesive layer so that the proximal face contacts the surgical site and so that each of the one or more percutaneous pins or wires extends through a respective one of the one or more slits. In some instances, more than one bandage may be used. Placing the adhesive layer at the surgical site causes the bandage to become attached to the surgical site, allowing the absorbent layer of the bandage to absorb fluids that may leak out of wounds at the surgical site, and allowing the antimicrobial agent to provide antimicrobial protection to the surgical site.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of protecting a surgical site with a plurality of percutaneous pins or wires from infection, the method comprising:
   providing a plurality of initially separate bandages for providing wound care at the surgical site, each bandage comprising:
      an adhesive layer with a first side configured to adhere to tissue and a second side opposite the first side;

a backing layer adjacent to the first side of the adhesive layer;
   an absorbent layer overlaying at least part of the second side of the adhesive layer, wherein the absorbent layer is a different material than the adhesive layer;
   an antimicrobial agent impregnated in or adjacent to at least one of the adhesive layer or the absorbent layer, wherein the antimicrobial agent comprises one or more of chlorhexidine, chlorhexidine gluconate, polyhexamethylene biguanide, honey, antibiotic, gentamicin, mupirocin, bacitracin, hypochlorous acid, gentian violet, essential oil, or tea tree oil; and
   a slit passing through the bandage;
   wherein the slit is configured to receive a percutaneous surgical pin or wire therethrough,
   wherein each bandage has a thickness in a range of about 0.5 cm to about 10 cm and a diameter or width in a range of about 2 cm to about 12 cm;
removing the backing layer from the first side of each bandage; and
placing the initially separate bandages at the surgical site such that the percutaneous pins or wires are received through corresponding slits of the bandages,
wherein the antimicrobial agent of each bandage protects the surgical site from infection,
wherein the adhesive layer of each bandage adheres the bandage to tissue at the surgical site,
wherein the absorbent layer of each bandage absorbs fluids that may leak from the surgical site,
wherein the bandages have one or more geometric shapes selected from circular, rectangular, triangular, pentagonal, hexagonal, or octagonal, wherein the initially separate bandages are placed in abutment to form a bandage system that covers the surgical site without significant gaps or overlap.

2. The method of claim 1, wherein the adhesive layer of each bandage comprises at least one of hydrocolloid, acrylic polymer film, cyanoacrylate film, or silicone film.

3. The method of claim 1, wherein the absorbent layer of each bandage comprises a porous and/or hydrophilic material and is configured to absorb fluids that may leak from the surgical site.

4. The method of claim 3, wherein the porous and/or hydrophilic material is impregnated with a hemostatic agent.

5. The method of claim 4, wherein the hemostatic agent is selected from the group consisting of thrombin, thrombin enzyme, prothrombin complex concentrate, dried plasma, cyanoacrylate, fibrin sealant, tranexamic acid, microfibrillar collagen, microporous polysaccharide spheres, gelatin matrix, oxidized regenerated cellulose, alginate, albumin, glutaraldehyde, alum, aluminum chloride, zinc chloride, and ferric sulfates.

6. The method of claim 1, wherein the thickness of each bandage is in a range of about 0.5 cm to about 5 cm, and wherein the adhesive layer of each bandage has a cross-sectional thickness in a range of about 0.1 mm to about 2 mm.

7. The method of claim 1, wherein each bandage further comprises a central opening through each of the adhesive layer and the absorbent layer in communication with the slit, wherein the central opening through the adhesive layer is larger than the central opening through the absorbent layer.

8. The method of claim 1, wherein the diameter or width of each bandage is in a range of about 2 cm to about 5 cm.

9. The method of claim 8, wherein the slit of each bandage passes across about 20% to about 80%, or about 30% to about 70%, or about 40% to about 60%, or about 45% to about 55%, of the diameter or width of the bandage.

10. The method of claim 1, wherein the one or more geometric shapes of the bandages facilitate placement of the bandages around the plurality of percutaneous pins or wires at the surgical site.

11. The method of claim 1, wherein the bandages are attached to tissue at the surgical site without the use of external fixtures.

12. The method of claim 1, wherein the antimicrobial agent of each bandage is provided in its own layer.

13. The method of claim 1, at least one of the bandages comprising:

a plurality of slits passing through the bandage, each slit extending from an outer edge or perimeter of the bandage toward an interior portion of the bandage.

14. The method of claim 13, wherein each slit passes through about 30% to about 70%, or about 40% to about 60%, or about 45% to about 55%, of the diameter or width of the bandage.

15. A method of protecting a surgical site with a plurality of percutaneous pins or wires from infection, the method comprising:

providing a plurality of initially separate bandages, each bandage comprising:

an adhesive layer with a first side configured to adhere to tissue and a second side opposite the first side;

a backing layer adjacent to the first side;

an absorbent layer adjacent to the second side;

an antimicrobial agent impregnated in or adjacent to at least one of the adhesive layer or the absorbent layer; and a slit passing through the bandage, wherein the slit is configured to receive a percutaneous surgical pin or wire therethrough;

removing the backing layer from the first side of each of the bandages; and placing the initially separate bandages at the surgical site such that percutaneous pins or wires are received through corresponding slits of the bandages, wherein the antimicrobial agent of each bandage protects the surgical site from infection;

wherein the adhesive layer of each bandage adheres the bandage to tissue at the surgical site; and wherein the absorbent layer of each bandage absorbs fluids that may leak from the surgical site, wherein the bandages have one or more geometric shapes selected from circular, rectangular, triangular, pentagonal, hexagonal, or octagonal, wherein the initially separate bandages are placed in abutment to form a bandage system that covers the surgical site without significant gaps or overlap.

16. The method of claim 15, wherein the adhesive layer of each bandage comprises at least one of hydrocolloid, acrylic polymer film, cyanoacrylate film, or silicone film;

wherein the absorbent layer comprises a porous material configured to absorb fluids that may leak from the surgical site;

wherein the antimicrobial agent is impregnated in the absorbent layer;

wherein a hemostatic agent is impregnated in the absorbent layer.

* * * * *